(12) United States Patent
Chen et al.

(10) Patent No.: US 7,956,189 B2
(45) Date of Patent: Jun. 7, 2011

(54) MALEATE, TOSYLATE, FUMARATE AND OXALATE SALTS OF 5-(1-(S)-AMINO-2-HYDROXYETHYL)-N-[(2,4-DIFLUOROPHENYL)-METHY]-2-[8-METHOXY-2-(TRIFLOUROMETHY)-5-QUINOLINE]-4-OXAZOLECARBOXAMIDE AND PREPARATION PROCESS THEREFORE

(75) Inventors: Xiaoming Chen, Westfield, NJ (US); Xiao Chen, Edison, NJ (US); Jianguo Yin, Plainsboro, NJ (US); Xiaoyong Fu, Edison, NJ (US); David J. Blythin, North Caldwell, NJ (US); Rongze Kuang, Green Brook, NJ (US); Ho-Jane Shue, Henderson, NV (US); Scott Trzaska, Raritan, NJ (US); Chee-Wah Tang, Singapore (SG); Vincenzo Liotta, Glen Ridge, NJ (US); Zaher Shabani, Budd Lake, NJ (US)

(73) Assignee: Schering Corporation, Kenilworth, NJ (US)

( * ) Notice: Subject to any disclaimer, the term of this patent is extended or adjusted under 35 U.S.C. 154(b) by 866 days.

(21) Appl. No.: 11/891,351

(22) Filed: Aug. 10, 2007

(65) Prior Publication Data

US 2008/0108818 A1     May 8, 2008

Related U.S. Application Data

(60) Provisional application No. 60/837,661, filed on Aug. 14, 2006.

(51) Int. Cl.
   *C07D 215/38* (2006.01)
(52) U.S. Cl. .......................................................... 546/167
(58) Field of Classification Search ................... 546/167
   See application file for complete search history.

(56) References Cited

U.S. PATENT DOCUMENTS 7,511,062 B2 *   3/2009   Kuang et al. ................. 514/312
2006/0106062 A1   5/2006   Kuang et al.

FOREIGN PATENT DOCUMENTS

WO         2005116009      * 12/2005
WO      WO 2005/116009      12/2005

OTHER PUBLICATIONS

Berge, J Pharm Sci, vol. 66, No. 1, pp. 1-17, 1977.*
International Search Report for PCT/US2007/017848; mailed Jan. 21, 2008, 3 pages.

* cited by examiner

*Primary Examiner* — D. Margaret Seaman
(74) *Attorney, Agent, or Firm* — Patricia A. Shatynski; Valerie J. Camara

(57) ABSTRACT

Disclosed are maleate, tosylate, fumarate, and oxalate salts of the compound 5-(1(S)-Amino-2-Hydroxyethyl)-N-[(2,4-Difluorophenyl)-Methyl]-2-[8-Methoxy-2-(Trifluoromethyl)-5-Quinoline]-4-Oxazolecarboxamide, represented by Formula I, and methods of preparing the same.

10 Claims, 29 Drawing Sheets

DSC

TGA

MALEATE, TOSYLATE, FUMARATE AND OXALATE SALTS OF 5-(1-(S)-AMINO-2-HYDROXYETHYL)-N-[(2,4-DIFLUOROPHENYL)-METHY]-2-[8-METHOXY-2-(TRIFLOUROMETHY)-5-QUINOLINE]-4-OXAZOLECARBOXAMIDE AND PREPARATION PROCESS THEREFORE

CROSS-REFERENCE TO RELATED APPLICATIONS

The present application claims the priority of U.S. Provisional Application No. 60/837,661 filed Aug. 14, 2006, which is incorporated herein by reference in its entirety.

FIELD OF THE INVENTION

This patent application generally relates to pharmaceutically useful salts and a novel process to prepare pharmaceutically useful salts. It specifically relates to pharmaceutically useful salts and a novel process to synthesize pharmaceutically useful salts of 5-(1(S)-amino-2-hydroxyethyl)-N-[(2,4-difluorophenyl)-methyl]-2-[8-methoxy-2-(trifluoromethyl)-5-quinoline]-4-oxazolecarboxamide.

BACKGROUND OF THE INVENTION

The preparation of 5-(1(S)-amino-2-hydroxyethyl)-N-[(2,4-difluorophenyl)-methyl]-2-[8-methoxy-2-(trifluoromethyl)-5-quinoline]-4-oxazolecarboxamide (the compound of Formula I) is disclosed in Published International WO 2005/116009 A1, filed on May 16, 2005 (the '009 publication), which is incorporated herein in its entirety.

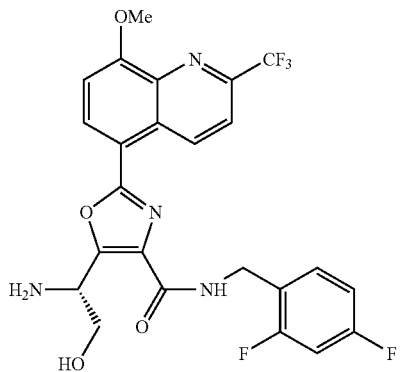

Formula I

The novel compounds disclosed in the '009 publication, including the compound of Formula I, are classified as PDE-4 inhibitor compounds and are useful therapeutic agents in the treatment of inflammatory conditions, for example COPD and Asthma.

As reported in the '009 publication, the compound of Formula I was characterized by TLC and by LC/MS techniques. The procedures described in the '009 publication yielded the compound of Formula I in a crystalline solid hydrochloride form. However the hydrochloride form isolated by this method is highly hygroscopic, making it difficult to process into a medicament.

In general, compounds which have been identified as having therapeutic activity must be provided in a highly pure form for pharmaceutical use. Moreover, it is also desirable to provide compounds intended for pharmaceutical use in a form such that it is handled easily for incorporation into a medicament. It is also desirably that compounds, in the form incorporated into a medicament, possesses a sufficiently robust character resistant to chemical degradation, and thereby imparts a long shelf life to the medicament.

OBJECTIVES AND SUMMARY OF THE INVENTION

In view of the foregoing, what is desired is a form of the therapeutic agent which lends itself to providing the therapeutic agent in a highly purified form. What is desired also is a form of the therapeutic agent which is robust toward degradation under the environmental conditions in which it is handled and stored.

These and other objectives are advantageously provided by the present invention, which in one aspect provides the compound of Formula I in a salt form which is crystalline, stable in the ambient environment and optionally incorporates one or more solvent molecules thereinto, for example, a crystalline monohydrate. In some embodiments the salt form of compound I is selected from a maleate salt form, a tosylate salt form, a fumarate salt form, and an oxalate salt form. In some embodiments the preferred salt form of compound I is a maleate monohydrate salt.

One aspect of the present invention is a process for the provision of a crystalline maleate monohydrate salt form of the compound of Formula I

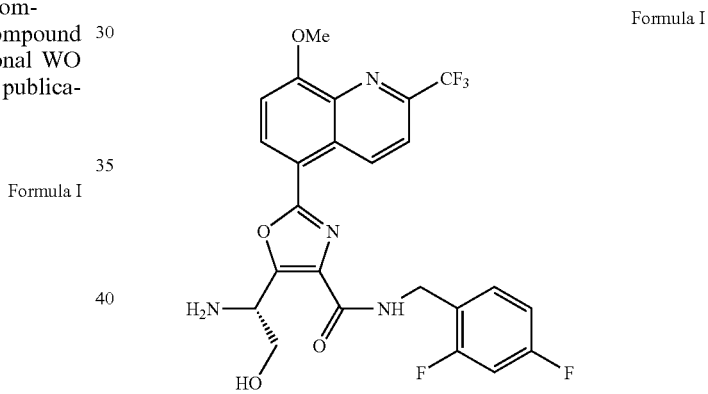

Formula I the process comprising:
(a) suspending an aliquot of the free base compound of Formula I in a mixed isopropanol/water solvent comprising at least 50 vol % i-propanol, wherein the ratio of suspended material to solvent is at least about 1:8 weight in g/vol in ml;
(b) heating the suspension prepared in step "a" to at least 50° C.;
(c) admixing over a 10 minute period with the heated suspension prepared in Step "b" a solution made by dissolving at least one equivalent of maleic acid in sufficient amount of a mixed solvent to dissolve it, the mixed solvent comprising 50% by volume i-propanol and 50% by volume water;
(d) filtering the admixture from Step "c" to provide a solution while maintaining the temperature of the solution at a temperature of at least about 50° C.;
(e) adding over a 10 minute period to the filtrate from Step "d" additionally about 1.25 volumes of water based on the volume of water used in Step "a" while maintaining the mixture at a temperature of at least about 50° C.;
(f) cooling the solution from Step "e" to about 40° C. over 30 minutes, thereby forming a precipitate slurry;

(g) stirring the slurry from Step "f" for a first period of time at a temperature of about 40° C., followed by cooling the slurry to 5° C. over a 2 hour period;

(h) optionally collecting the solids precipitated in Step "g" and washing them in a mixed isopropanol/water solvent containing at least 66% isopropanol by volume;

(i) optionally drying the solids obtained in step "h" in a vacuum oven for 5 hours at 55° C.

Another aspect of the present invention a crystalline maleate monohydrate salt of 5-(1(S)-amino-2-hydroxyethyl)-N-[(2,4-difluorophenyl)-methyl]-2-[8-methoxy-2-(trifluoromethyl)-5-quinoline]-4-oxazolecarboxamide (maleate monohydrate compound of Formula II) in accordance with the above-described process, which salt

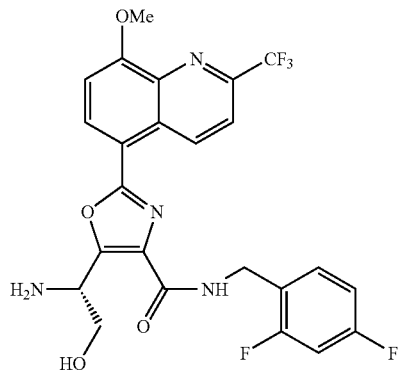

Formula I

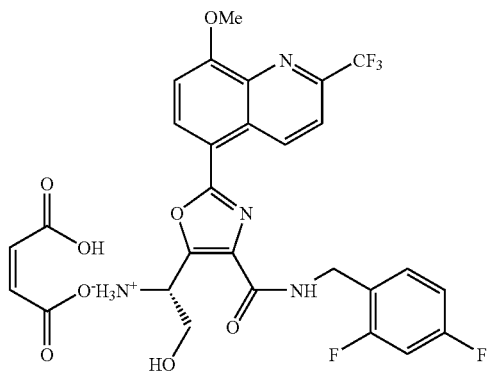

Formula II is characterized by Proton NMR analysis ($^1$H NMR, 400 MHz, DMSO) having the following chemical shift data: 10.17 (d, 1H), 9.40 (t, 1H), 8.30 (b, 3H), 8.5 (d, 1 H), 8.05 (d, 1H), 7.58 (d, 1H), 7.45 (dd, 1H), 7.12 (dd, 1H), 7.05 (dd, 1H), 6.02 (s, 2H), 5.65 (b, 1H), 5.15 (t, 1H), 4.60 (m, 2H), 4.13 (s, 3H), 3.90 (m, 2H), and which crystalline form is characterized by the Infrared Spectrum schematically illustrated in FIG. 10 and by an X-ray powder diffraction pattern shown in Table I expressed in terms of diffraction angle (in 2 θ, all values reflect an accuracy of ±0.2) lattice "d" spacing (in angstroms) and relative peak intensities ("RI"):

TABLE I

| Diffraction angle (2 θ, ±0.2) | RI | Lattice Spacing (Å ± 0.04) |
|---|---|---|
| 6.5 | Strong | 13.59 |
| 7.5 | Very Strong | 11.78 |
| 21.2 | Very Strong | 4.19 |
| 27.2 | Very Strong | 3.28 |

One aspect of the present invention is a process for the provision of a crystalline tosylate hydrate salt form I of the compound of Formula I the process comprising:

(a) preparing an anhydrous crystalline tosylate salt by:

(1) suspending an aliquot of the free base compound of Formula I in at least 10 ml of acetonitrile/g of the compound of Formula I suspended;

(2) heating the suspension prepared in Step "a" to a temperature of at least about 60° C.;

(3) mixing at least one equivalent of toluenesulfonic acid into the suspension;

(4) heating the mixture prepared in Step "c" to at least about 70° C. yielding a solution;

(5) mixing t-butylmethyl ether into the hot solution prepared in Step "d" over a period of at least about 20 minutes in an amount that provides a ratio of 13:8 acetonitrile:t-butylmethylether in the mixture; and (6) cooling the mixture to ambient temperature over a period of at least about 2 hours precipitating the crystalline anhydrous toluenesulfonate (tosylate) salt of the compound of Formula I;

(b) collecting an aliquot of the precipitate salt prepared in Step "a(6)" and combining it with an amount of water to give a ratio of 6 ml of water/g of salt for a period of time necessary to produce a first solid scum;

(c) slurrying the solid scum produced in Step "b" with an amount of water equal to 1.66× the amount of water used in Step "b";

(d) agitating the slurry prepared in Step "c" for a period of time necessary to produce a wet cake;

(e) adding an additional 3× the amount of water added in Step "c" to form a second slurry with the wet cake produced in Step "d" and agitating the slurry for 5 days;

(f) drying the solids from the slurry produced in Step "e" under vacuum at ambient temperature, thereby producing the toluenesulfonate hydrate Form I salt form of the compound of Formula I.

Another aspect of the present invention is the provision of a crystalline tosylate hydrate salt Form I of 5-(1(S)-amino-2-hydroxyethyl)-N-[(2,4-difluorophenyl)-methyl]-2-[8-methoxy-2-(trifluoromethyl)-5-quinoline]-4-oxazolecarboxamide (tosylate trihydrate compound of Formula IV) in accordance with the above-described procedure, Formula IV

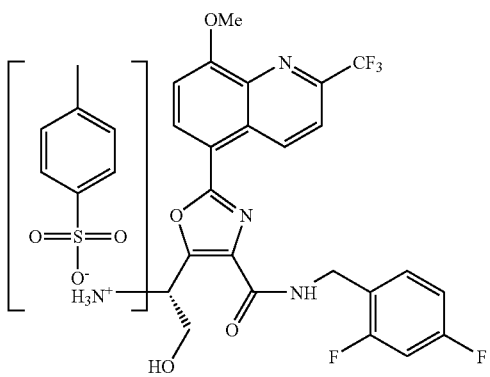

which crystalline salt form is characterized by the Infrared Spectrum schematically illustrated in FIG. 11 and by the X-ray powder diffraction pattern shown in Table II expressed in terms of diffraction angle (in 2 θ, all values reflect an accuracy of ±0.2) lattice "d" spacing (in angstroms) and relative peak intensities ("RI"):

TABLE II

| Diffraction angle (2θ, ±0.2 | RI | Lattice Spacing (Å ± 0.04) |
|---|---|---|
| 5.2 | Weak | 16.98 |
| 12.5 | Medium | 7.08 |
| 20.0 | Weak | 4.44 |
| 26.3 | Strong | 3.39 |

Another aspect of the present invention is a method for the preparation of a crystalline fumarate salt form of 5-(1(S)-amino-2-hydroxyethyl)-N-[(2,4-difluorophenyl)-methyl]-2-[8-methoxy-2-(trifluoromethyl)-5-quinoline]-4-oxazolecarboxamide (fumarate salt compound having the structure of Formula V), Formula V

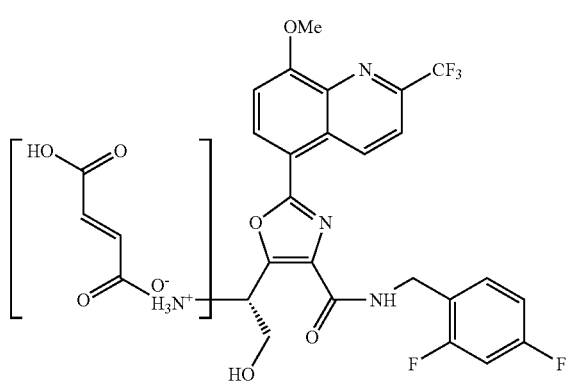

by the process comprising:
(a) suspending an aliquot of the free base compound having the structure of Formula I in 50 ml of acetonitrile;
(b) heating the suspension formed in Step "a" to about 60° C.;
(c) mixing with the heated suspension at least one equivalent of fumaric acid;
(d) heating the mixture prepared in Step "c" to a temperature at which the suspended materials are dissolved;

(e) cooling the solution prepared in Step "d" to ambient temperature over a period of about 2 hours to provide a precipitate; and
(f) collecting the precipitate and drying it in a vacuum oven at a temperature of about 50° C.

In some embodiments it is preferred for the mixture in Step "d" to be heated to at least about 80° C. In some embodiments the preferred ambient temperature is about 25° C.

Another aspect of the present invention is the provision of a crystalline fumarate salt form of 5-(1(S)-amino-2-hydroxyethyl)-N-[(2,4-difluorophenyl)-methyl]-2-[8-methoxy-2-(trifluoromethyl)-5-quinoline]-4-oxazolecarboxamide prepared in accordance with the above-described method, which crystalline form is characterized by the X-ray powder diffraction pattern shown in Table III expressed in terms of diffraction angle (in 2 θ, all values reflect an accuracy of ±0.2) lattice "d" spacing (in angstroms) and relative peak intensities ("RI"):

TABLE III

| Diffraction angle (2θ, ±0.2 | RI | Lattice Spacing (Å ± 0.04) |
|---|---|---|
| 8.0 | Strong | 11.04 |
| 19.9 | Medium | 4.46 |
| 22.5 | Medium | 3.95 |
| 25.6 | Medium | 3.48 |

BRIEF DESCRIPTION OF THE FIGURES

FIG. 11b containing the spectrum expanded over the region from 0.1600 cm$^{-1}$ to 900 cm$^{-1}$, and FIG. 11c containing the spectrum expanded over the region from 900 cm$^{-1}$ to 200 cm$^{-1}$ [Vertical Axis: % transmittance; Horizontal Axis: wave numbers in cm$^{-1}$].

DETAILED DESCRIPTION OF THE INVENTION

Figure 1:
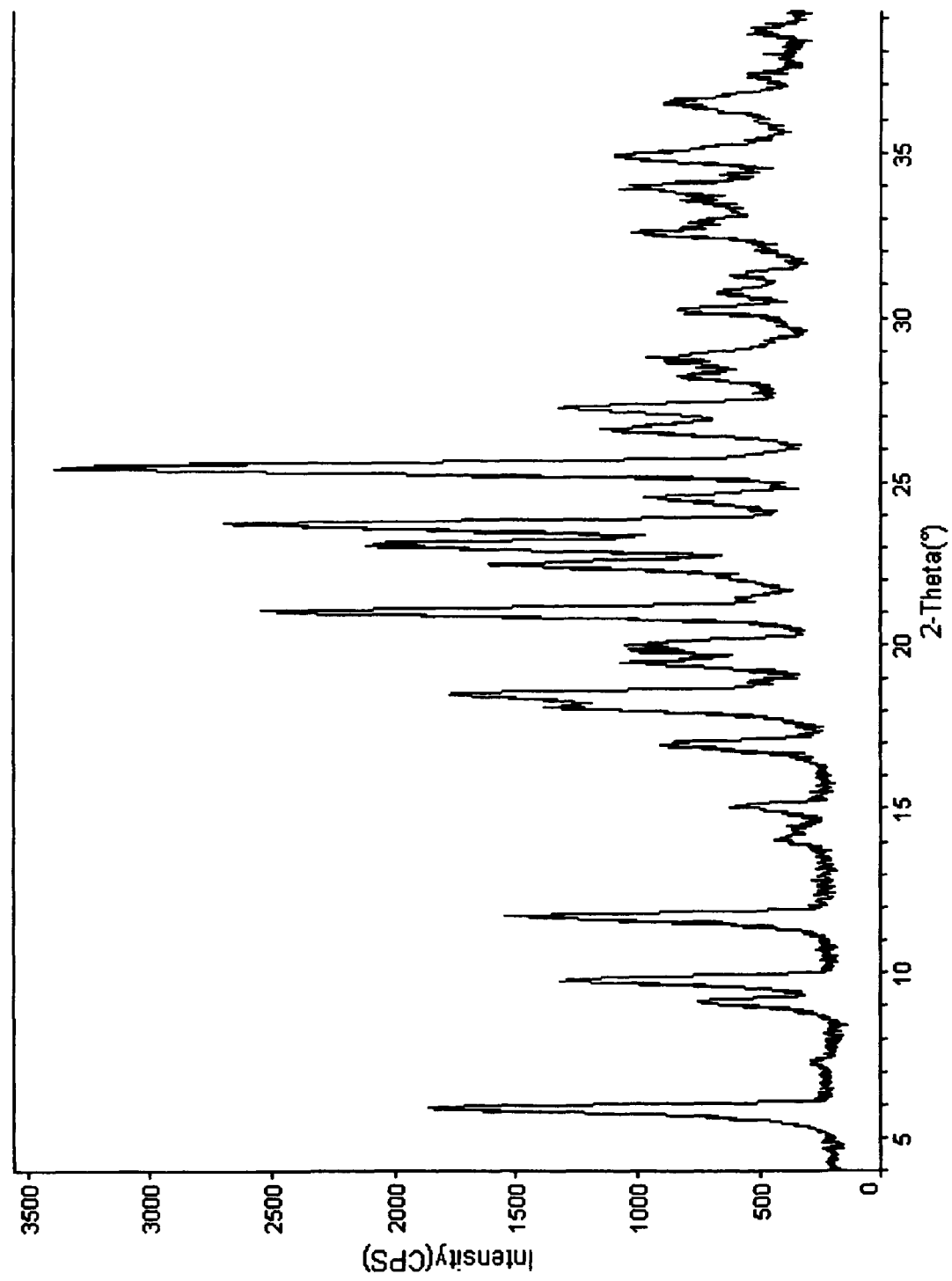
FIG. 1 presents a characteristic x-ray powder diffraction pattern of the crystalline anhydrous maleate salt form of the compound of Formula I [Vertical Axis: Intensity CPS, counts (square root)); Horizontal Axis: Two Theta (degrees)].

Salt forms of 5-(1(S)-amino-2-hydroxyethyl)-N-[(2,4-difluorophenyl)-methyl]-2-[8-methoxy-2-(trifluoromethyl)-5-quinoline]-4-oxazolecarboxamide (the compound of Formula I), also termed 5-(1(S)-amino-2-hydroxyethyl)-N-[(2,4-difluorophenyl)-methyl]-2-[8-methoxy-2-(trifluoromethyl)-quinolin-5-yl]-4-oxazolecarboxamide

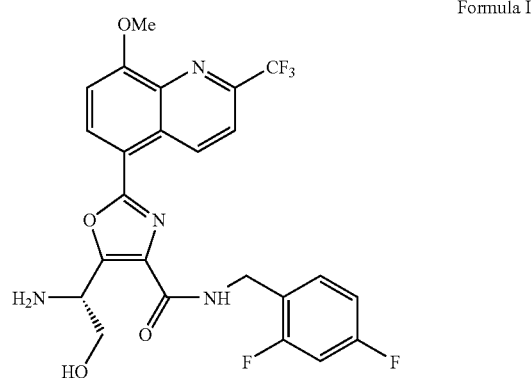

Formula I have useful pharmaceutical activity as PDE IV inhibitor compounds. The salt forms of the compound of Formula I disclosed herein have processing advantages when compared to the free base of Formula I related to one or more of their improved solubility in at least one solvent, improved chemical stability, improved physical stability in the ambient environment, and improved thermal stability. These improved properties are beneficial in the provision of useful medicaments. Moreover, each of the maleate, the tosylate, and the fumarate salts have one or more crystalline forms which provide the compound of Formula I in a form having the following advantages compared to other forms of the compound: lower impurity content and more consistent product quality i.e., more consistent physical characteristics including more consistent color, rate of dissolution and ease of handling; as well as a longer term stability when incorporated into a medicament.

As described in detail below, each of the crystalline salt forms of the compound of Formula I described herein can readily be distinguished from one another and from amorphous forms by examination of one or more of the characteristic X-ray Diffraction patterns (see FIGS. 1, 4, 7, 10, 12, 15, 18, 21, and 24), characteristic infrared spectra (see FIGS. 10 and 11), the characteristic analytical Differential Scanning Calorimetry (DSC) thermograms (FIGS. 2, 5a, 5b, 8, 13, 16, 19, 22, and 25), and the characteristic thermogravimetric analysis (TGA) thermograms (FIGS. 3, 6, 9, 14, 17, 20, 23 and 26) of the respective salt forms.

The inventors have been the first to recognize that the primary amine functionality pendent on the left side of the oxazoline ring of the compound of Formula I as depicted above, can alone be protonated to provide a salt compound of Formula III having desirable physical and stability properties, Formula III

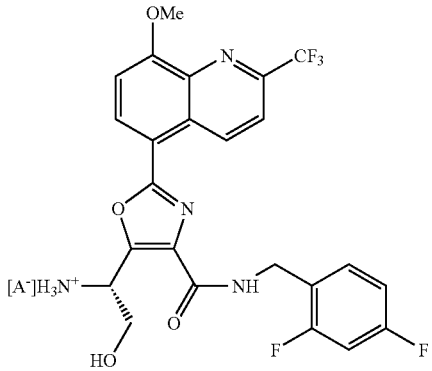

where "A⁻" is an anionic moiety, for example, mesylate, fumarate, maleate, tosylate, sulfate, oxalate, phosphate, and chloride.

The inventors have also been the first to recognize that certain crystalline salt forms, described in detail below, incorporating one or more molecules of solvent, for example, water, ethanol and methanol, for each molecule of the protonated compound of Formula I provides a crystalline form of the compound having desirable handling and stability properties in comparison to the compound of Formula I.

Preferred crystalline forms of the salt are thermodynamically robust, in that they are not converted into other forms when handled and stored in ordinary environments, are thermally stable, and in addition to having desirable solubility and handling characteristics, thus providing the compound of Formula I in a salt form which is easily incorporated into a medicament and which is stable under a wide variety of environmental conditions.

As is known, therapeutic agents typically display poor absorption rates when they have an aqueous solubility of less than about 10 mg/ml over a pH range of from about pH 1 to about pH 7. Moreover, when orally administered therapeutic agents display a solubility of less than about 1 mg/ml within this pH range, typically such agents exhibit dissolution-rate limited absorption since solubility and absorption are related in orally administered medicaments. Some of the salts disclosed herein have improved solubility properties in comparison with the free base compound of Formula I. Accordingly, the improved solubility properties of these salts are important for the provision of an orally administered form of a medicament designed to deliver the compound of Formula I as a therapeutic agent. In addition to these desirable improved solubility properties, as described in detail below, selected salts displayed additional advantageous physical properties.

In general, the compound salt is prepared from a compound of Formula I and an acid selected from fumaric acid, hydrochloric acid, maleic acid, methylsulfonic acid, oxalic acid, phosphoric acid, sulfuric acid, and toluenesulfonic acid. Unless noted otherwise below, the acid salts were prepared in accordance with the following procedure:

i) Suspend a weighed amount of the free base in a solvent with stirring;
ii) add a measured amount of acid or acid solution;
iii) heat mixture to a temperature above ambient to dissolve the suspended materials and cool to ambient to precipitate the salt; and
iv) optionally, recrystallize collected salt.

The salts prepared in this manner were analyzed by a number of techniques

Analytical Procedures

Each of the crystalline salt forms of the compound of Formula I is characterized by one or more techniques including X-ray powder diffraction spectroscopy (PXRD), differential scanning calorimetry (DSC), thermogravimetric analysis (TGA) and/or further characterized by physical methods including solubility studies and stability studies.

Infrared Spectroscopy

Samples were characterized utilizing attenuated total reflectance (ATR) infrared spectroscopy using a Nicolet Instruments NEXUS 670 FTIR equipped with an Avatar Smart Miracle Attenuated Total Reflectance (ATR) sample compartment. Spectra were collected utilizing the following parameters: DTGS KBr Detector; KBr beam splitter; scanning range 600 cm−1 to 4000 cm−1; aperture setting 100; resolution 2; 64 scans/sample. The analysis was carried out by collecting a background spectrum, then placing reference standard or particulate sample (typically 3 mg to 5 mg of sample) on the ATR crystal and applying force to the sample with the instrument's pressure arm in accordance with the manufacturers recommendations. A spectrum of the specimen (reference or sample) was then obtained as a ratio of the background and specimen spectra utilizing the manufacturers proprietary software.

For some samples Fourier Transform Infrared (FTIR) spectra was obtained using a Nexus 670 FT-IR in transmission mode. Samples were dispersed in a KBr matrix and spectra were collected utilizing the following parameters: DTGS KBr Detector; KBr beam splitter; scanning range 400 cm−1 to 4000 cm−1; aperture setting 100; resolution 4; 32 scans/sample. Data was analyzed using software provided by the manufacturer.

X-Ray Powder Diffraction Spectroscopy

X-ray powder diffraction spectroscopy was obtained on samples using one of the following procedures.

For analysis of samples obtained using a Rigaku Miniflex spectrometer, the following procedure was employed (PXRD method I). Specimens analyzed by PXRD method I were lightly packed onto a low-background plate. The specimens were exposed to the room environment with ambient temperature and humidity. The Rigaku spectrometer was equipped with a six-plate carousel that rotated the specimen at 54 rpm, minimizing preferred orientations of the crystals in the sample studied. The Rigaku spectrometer was equipped also with a copper Kα radiation source utilized without a Kα2 filter. The spectrometer was equipped also with a variable divergence slit and 0.3 mm receiving slit. Scan range was carried out from 2.0 to 40°2θ. Instrument calibration was verified using the Cu Kα1 peak for the 111 plane. During scanning, the step size was 0.02 degrees over step durations of 0.6 seconds. Data analysis was accomplished using Jade Plus (release 5.0.26) analysis software. The data ware smoothed with a Savitzky-Golay parabolic filter at 11 points. Typically "d" spacing values are accurate to within ±0.04 A.

X-ray Powder Diffraction spectroscopy analysis was obtained for some samples using a Bruker D8 diffractometer. The Bruker diffractometer was equipped with a parallel optic configuration utilizing a GÖBEL beam focusing mirror and a PSD detector equipped with a fixed radial soller slit. The Bruker diffractometer was used with an Anton Paar TTK450 temperature stage. The radiation source is copper (Kα). The divergence slits are fixed at 0.6 mm. The Bruker diffractometer utilized a top-loading brass block sample holder. PSD fast scan was used to scan from 4.0° to 39.9°. To obtain a diffraction pattern, specimens were loaded onto the sample holder and leveled with a glass microscope slide. The sample chamber temperature was set at 25° C., 30° C. or 120° C., under ambient humidity and not purged with nitrogen and not under vacuum. Instrument calibration was verified using mica standards. During scanning, the step size was 0.013 degrees to 0.02 degrees over step durations of 0.5 to 10 seconds. Data analysis was accomplished using EVA analysis software, version 7.0.0.1, supplied by Bruker® written by SOCABIM®. The data were smoothed by the software at 0.1 to 0.15.

X-ray Powder Diffraction spectroscopy analysis was obtained for some samples using a Shimadzu XRD-6000 X-ray diffractometer equipped with a copper Kα radiation source. Samples were analyzed from 2.0 to 40.0°2 θ (theta) with a step size of 0.02 degrees over step durations of 0.6 seconds. Data analysis was conducted using Basic Process software, version 2.6, supplied by Shimadzu. The data was smoothed using the automatic smoothing process in the software Samples for analysis by X-ray Powder Diffraction ("PXRD"). were subjected to minimal preparation to prevent any form changes. Sample particles were lightly packed into the sample holder to insure that they formed a smooth surface and did not clump together. No solvents, drying or other preparation steps were used for other than the solvate samples prepared in accordance with the procedure described above.

Differential Scanning Calorimetry

Calorimetric studies were conducted utilizing a modulated Differential Scanning Calorimeter (DSC) from TA instruments. Unless otherwise noted, DSC scans were performed at a heating rate of 10° C./min. using a hermetic pan with a pinhole lid and a nitrogen purge of 40 ml/min. Some analyses were performed at a heating rate of 2° C./min using an open aluminum pan under nitrogen flowing at a rate of 40 ml/min.

Solubility tests were conducted by placing an excess of the compound in an aliquot of the solvent of interest and allowing the slurry to equilibrate under the selected temperature conditions (typically ambient). When the solvent was water, pH was adjusted to the desired value with hydrochloric acid and sodium hydroxide. When the slurry mixture had equilibrated, the excess solids were centrifuged (water) or filtered (all other solvents) from the supernatant and the amount of compound which had been dissolved was quantified utilizing HPLC analysis of diluted aliquots of the supernatant liquid. Pharmaceutical grade solvents were employed.

Chemical stability tests were carried out on aliquots of the salt form of interest by placing a accurately weighed sample of the salt form of the compound of Formula I into a polyethylene bag. The bagged samples were enclosed in fiberboard tubes fitted with metal caps which were stored under the indicated conditions of humidity and temperature for the indicated time. Analysis was carried out by dissolving the contents of a vial and quantifying the amount of solute utilizing HPLC analysis. Where noted the aliquots were stored in capped amber vials under the conditions noted instead of polyethylene bags.

EXAMPLES

Maleate salts (3 forms), fumarate salt, oxalate salt and tosylate salts (3 forms) of the compound of Formula I were prepared as described below. Each of the salt forms of the compound of Formula I were also characterized by one or more of the following spectroscopic techniques, including X-ray Powder Diffraction Spectroscopy, differential scanning calorimetry (DSC), thermogravimetric analysis (TGA), Infrared Spectroscopy and NMR spectroscopy using the procedures described above. Selected salt forms were analyzed for stability, solubility and other improved physical properties in accordance with the above-described procedures.

The free base compound of Formula I for use in preparing each of the salts discussed below was itself prepared from crude hydrochloride salt prepared in accordance with the procedures disclosed in pending Published International WO 2005/116009 A1, filed on May 16, 2005 (the '009 publication). All reactive crystallizations, recrystallization, and slurry procedures were carried out in commercially available solvents of the specified grade (generally pharmaceutical or food grade unless otherwise specified) and used as received (unless otherwise specified).

Maleate Salts of the Compound of Formula I

Preparation of Anhydrous Maleate Form 1 Salt Form

An 11.0 g (21.1 mmol) aliquot of the compound of Formula I (free base form) was suspended in 160 ml of acetonitrile. The suspension was heated to 60° C. and 3.2 g (27.6 mmol, 1.31 eq.) of maleic acid was added to the suspension. When the acid addition was complete a solution was obtained followed by precipitation of the salt. The solution over precipitate mixture was then heated up to reflux and about 80 ml of solvent was removed by distillation at one atmosphere. After concentrating the mixture it was cooled to 65° C. and 80 ml of t-butyl methylether was added over a 20 minute period using an additional funnel. The resulting suspension was cooled to 5° C. over two hours. Crystalline solids precipitated which were collected by filtration and dried in a vacuum oven at 50° C. for 10 hours, to give 11.1 g (81.6%) white needles. The dried crystals were analyzed by X-ray powder diffraction spectroscopy (FIG. 1), differential scanning calorimetry (FIG. 2) and thermogravimetric analysis (FIG. 3) according the above-described procedures. Proton NMR analysis ($^1$H NMR, 400 MHz, DMSO) gave the following chemical shift data: 10.17 (d, 1H), 9.40 (t, 1H), 8.30 (b, 3H), 8.5 (d, 1H), 8.05 (d, 1H), 7.58 (d, 1H), 7.45 (dd, 1H), 7.12 (dd, 1H), 7.05 (dd, 1H), 6.02 (s, 2H), 5.65 (b, 1H), 5.15 (t, 1H), 4.60 (m, 2H), 4.13 (s, 3H), 3.90 (m, 2H).

Thermal analysis reveals that it is an anhydrous form with melting point of 191° C. (FIG. 9, 10), which corresponds to a sharp endotherm about 191° C. in DSC. No significant weight loss was observed before 175° C.

X-ray powder diffraction spectroscopy was obtained on a sample of the maleate salt (FIG. 1) which exhibits absorption peaks at the following diffraction angles having the intensity shown in Table IV:

TABLE IV

| Peak position (2-θ) | Intensity (CPS) |
|---|---|
| 5.9 | 1667 |
| 7.3 | 85 |
| 9.1 | 558 |
| 9.8 | 1065 |
| 11.7 | 1322 |
| 14.0 | 189 |
| 14.4 | 159 |
| 15.0 | 381 |
| 16.9 | 637 |
| 18.1 | 1017 |
| 18.5 | 1411 |
| 19.5 | 679 |
| 20.0 | 684 |
| 21.0 | 2177 |
| 22.5 | 942 |
| 23.0 | 1527 |
| 23.7 | 2148 |
| 24.5 | 526 |
| 25.4 | 2998 |
| 26.6 | 739 |
| 27.2 | 863 |
| 28.2 | 365 |
| 28.8 | 569 |
| 30.2 | 407 |
| 30.7 | 303 |
| 31.2 | 240 |
| 32.6 | 529 |
| 32.9 | 241 |
| 33.5 | 239 |
| 33.9 | 502 |
| 34.9 | 594 |
| 36.4 | 489 |
| 37.2 | 140 |
| 38.5 | 217 |

Of the peaks appearing in the spectrum shown in FIG. 1, Table V below lists the 12 most characteristic peaks of the X-ray Powder Diffraction spectrum, expressed in diffraction angle expressed in degrees 2 theta (2 θ), the corresponding "d" spacing in angstroms (A), and relative intensities of the signal ("RI") in the following notation: S=strong, M=medium, W=weak; V=Very and D=diffuse, as shown in Table V below:

TABLE V

| Diffraction Angle (°2 θ ± 0.2) | d spacing (A, ±0.04) | relative intensity |
|---|---|---|
| 5.9 | 14.97 | S |
| 9.1 | 9.71 | W |
| 9.8 | 9.02 | M |
| 11.7 | 7.56 | S |
| 15.0 | 5.90 | W |
| 16.9 | 5.24 | W |
| 18.5 | 4.79 | S |
| 20.0 | 4.44 | W |
| 21.0 | 4.23 | VS |
| 23.7 | 3.75 | VS |
| 25.4 | 3.50 | VS |
| 27.2 | 3.28 | M |

Of the 12 peaks characteristic of the maleate Form I salt of the compound of Formula I shown in Table V, the eight most characteristic peaks are those appearing at diffraction angles (in °2 θ equal to 5.9, 9.8, 11.7, 16.9, 18.5, 21.0, 23.7, and 25.4, and the four most characteristic peaks are those appearing at diffraction angles (in °2 θ) equal to 5.9, 11.7, 21.0, and 25.4.

Figure 2:
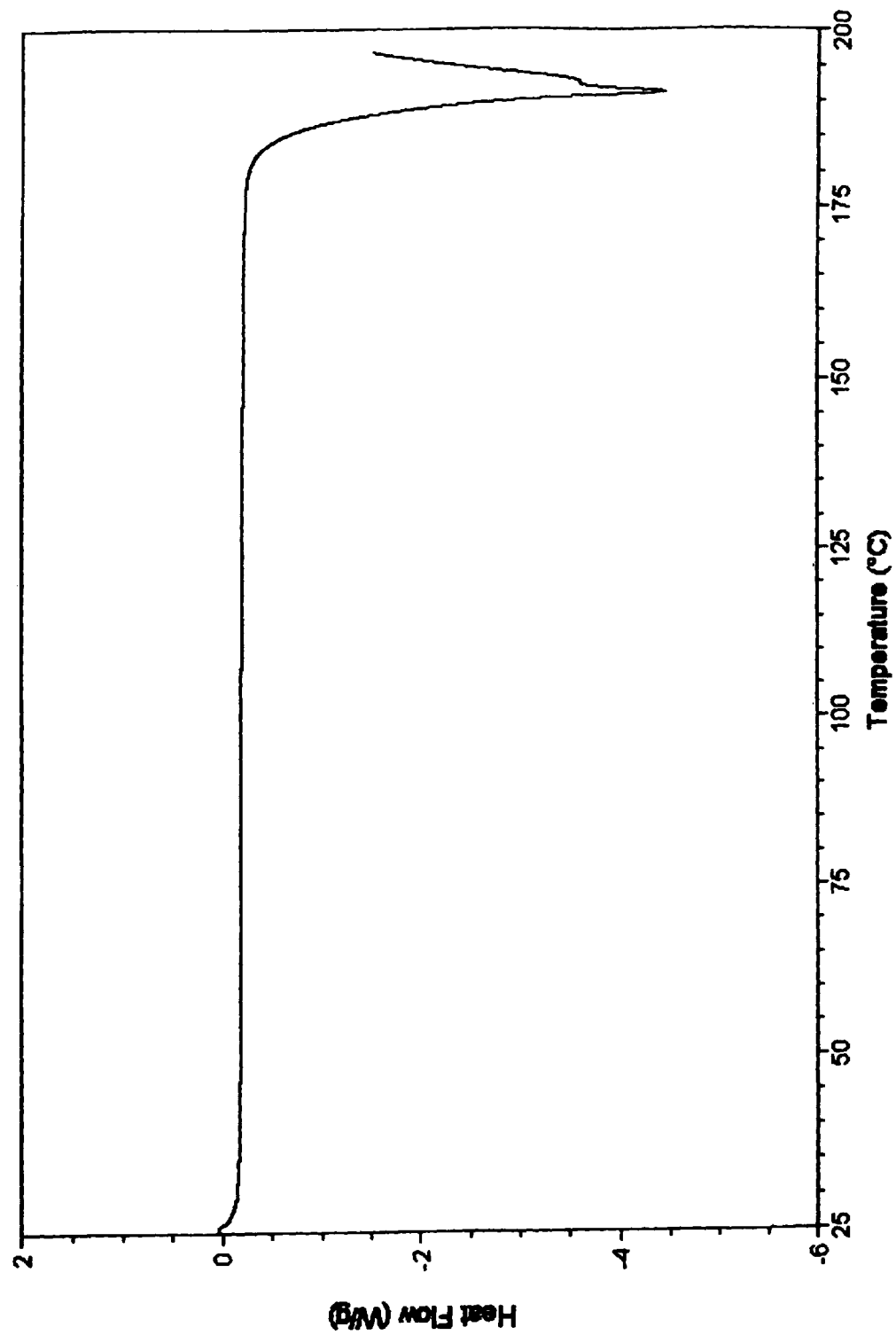
FIG. 2 presents a characteristic differential scanning calorimetry (DSC) thermogram of the crystalline anhydrous maleate salt form of the compound of Formula I, [Vertical Axis; Heat Flow in cal/sec/g; Horizontal Axis: Temperature in degrees centigrade].
Figure 3:
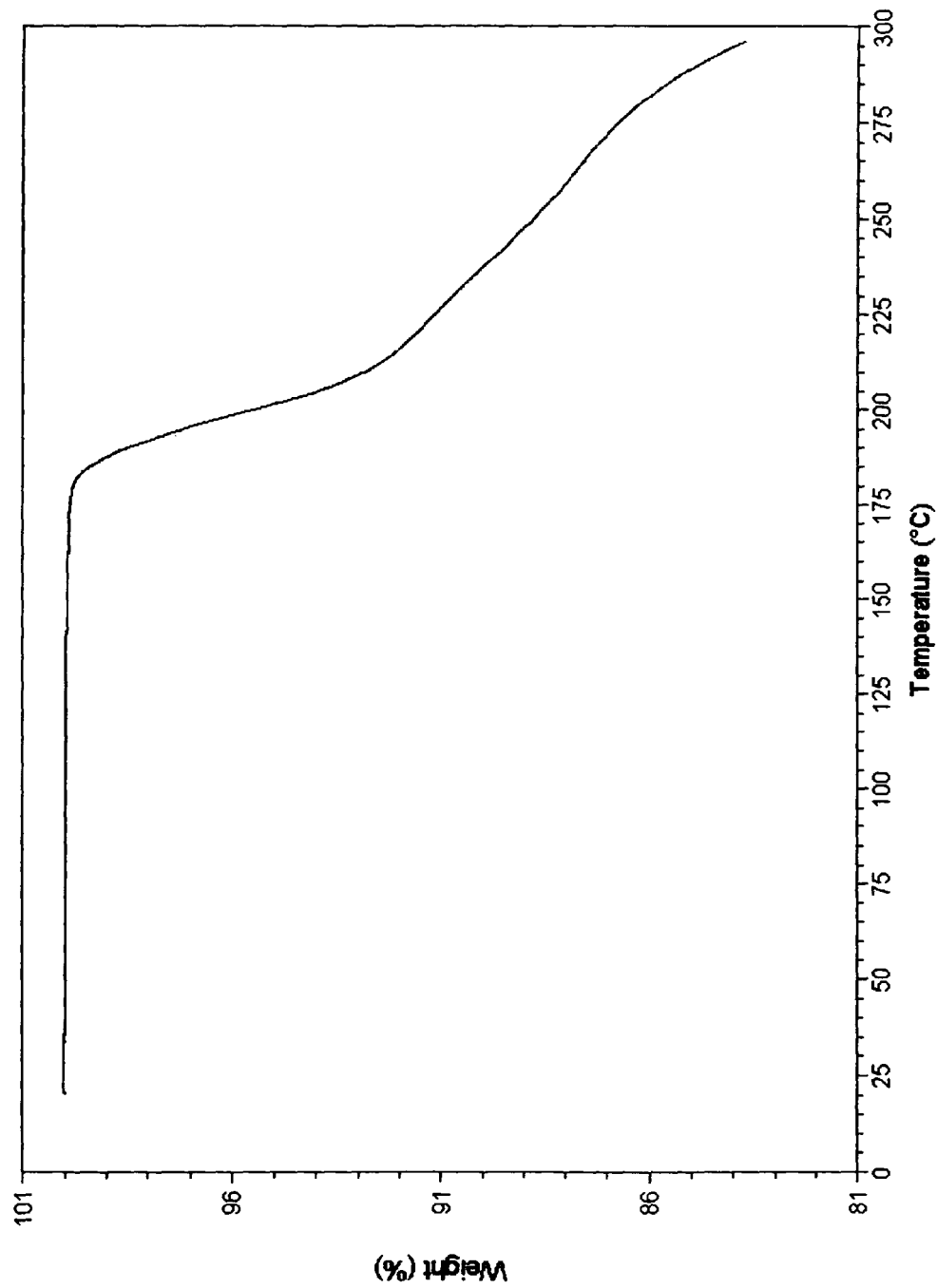
FIG. 3 presents a characteristic thermogravimetric analysis (TGA) of the crystalline anhydrous maleate salt form of the compound of Formula I, [horizontal axis; temperature, ° C., vertical axis; percent weight loss in sample].

FIG. 2 illustrates a DSC thermogram of the maleate Form I anhydrous salt form of the compound of Formula I, obtained in accordance with the above-described procedures, and FIG. 3 illustrates thermogravimetric analysis of the maleate anhydrous Form I salt form. This thermal analysis establishes that the salt is anhydrous with a melting point of 191° C. (corresponding to a sharp endotherm at 191° C. in the DSC). Moreover, it indicates that the salt is stable to about 175° C. with the TGA showing no significant weight loss below that temperature.

Preparation of Maleate Monohydrate Form 1 Salt Form

Method A:

An aliquot of the compound of Formula I (10.0 g, 19.2 mmol) was suspended in a solvent comprising a mixture of 40 ml. of isopropanol and 40 ml. of water. The suspension was heated to 50° C. To this suspension was added, over a 5 minute period while maintaining the suspension at 50° C., a solution comprising 2.9 g (1.3 equivalents) of maleic acid dissolved in a solvent comprising 10 ml of isopropanol and 10 ml of water heated to 50° C. The mixture was filtered at temperature and another 50 ml of water heated to 50° C. was added to the filtrate. After filtration, the solution was cooled, with stirring, over a 30 minute period to 40° C. The solution was stirred for 30 minutes, precipitating crystalline needles. The stirring was discontinued and the solution was cooled to 5° C. over a period of 2 hours, forming the crystalline maleate monohydrate Form 1 salt. After 2 hours the precipitate was collected by vacuum filtration, the filter cake was washed with a mixture comprising 10 ml isopropanol and 20 ml water, and dried in a vacuum oven for 10 hours at 50° C.

In some embodiments, it is preferred to use a 50:50 volumetric ratio of water:i-propanol as the solvent and slurry matrix. In some embodiments it is preferred to use a solvent comprising about 65 vol % i-propanol. In some embodiments it is preferred to use a solvent having a water content of from about 50 vol % to about 70 vol % water, preferably from about 50 vol. % to about 65 vol. % water, and more preferably from about 55 vol. % to about 65 vol. % water.

Method B:

A 27.0 g (51.7 mmol) aliquot of the compound of Formula I (free base form) was suspended in a mixture of 120 ml of n-propanol and 90 ml of water. The suspension was heated to 50° C. A solution of 8.7 g maleic acid (75.0 mmol, 1.45 eq.) in a mixture of 30 ml n-propanol and 30 ml of water was added over a 10 minute period to the heated suspension, resulting in dissolution of the suspend material. Over a 10 minute period an additional 180 ml of water was added to the solution using an addition funnel while maintaining the solution at 50° C. The solution was then cooled to 40° C. over 30 minutes, precipitating the monohydrate salt. The suspension was stirred for one hour at 40° C., followed by cooling to 5° C. over 2 hours. The solids were collected by filtration and dried in a vacuum over for 5 hours at 55° C., to give 32.8 g (96.6%) off-white needles. The water content of the dried needles was analyzed by Karl Fischer titration. The analysis showed that the water content was 2.8% (theoretical 2.7% for monohydrate).

The dried crystals of maleate monohydrate Form I salt form produced by Method B were analyzed by infrared spectroscopy (FIG. 10), X-ray powder diffraction spectroscopy (FIG. 1), differential scanning calorimetry (FIG. 2) and thermogravimetric analysis (FIG. 3) according the above-described procedures. Elemental analysis was conducted, Anal. calcd. for $C_{28}H_{25}F_5N_4O_9$ (monohydrate 656.5): C, 51.25; H, 3.84; N, 8.53. Found: C, 51.27; H, 3.5 9; N, 8.54.

X-ray powder diffraction spectroscopy was obtained on a sample of the maleate monohydrate Form I salt (FIG. 4) which exhibits absorption peaks at the following diffraction angles having the intensity shown in Table VI:

TABLE VI

| Peak position (2-Theta) | Intensity (CPS) |
| --- | --- |
| 6.5 | 1682 |
| 7.5 | 2385 |
| 9.1 | 246 |
| 10.4 | 886 |
| 12.3 | 640 |
| 12.8 | 531 |
| 13.5 | 216 |
| 14.8 | 1963 |
| 15.2 | 321 |
| 15.8 | 390 |
| 16.1 | 472 |
| 17.0 | 302 |
| 17.3 | 605 |
| 18.2 | 623 |
| 19.2 | 681 |
| 20.0 | 577 |
| 20.3 | 402 |
| 21.2 | 3247 |
| 21.6 | 223 |
| 22.2 | 2710 |
| 23.2 | 1300 |
| 23.6 | 260 |
| 24.6 | 232 |
| 24.8 | 426 |
| 25.6 | 3689 |
| 26.3 | 425 |
| 27.2 | 5114 |
| 27.9 | 195 |
| 28.7 | 232 |
| 29.6 | 334 |
| 30.1 | 480 |
| 30.9 | 307 |
| 31.5 | 852 |
| 32.3 | 796 |
| 32.9 | 142 |
| 34.2 | 541 |
| 34.5 | 581 |
| 34.9 | 381 |
| 36.5 | 248 |
| 37.1 | 1107 |
| 37.7 | 282 |
| 38.9 | 692 |

Figure 4:
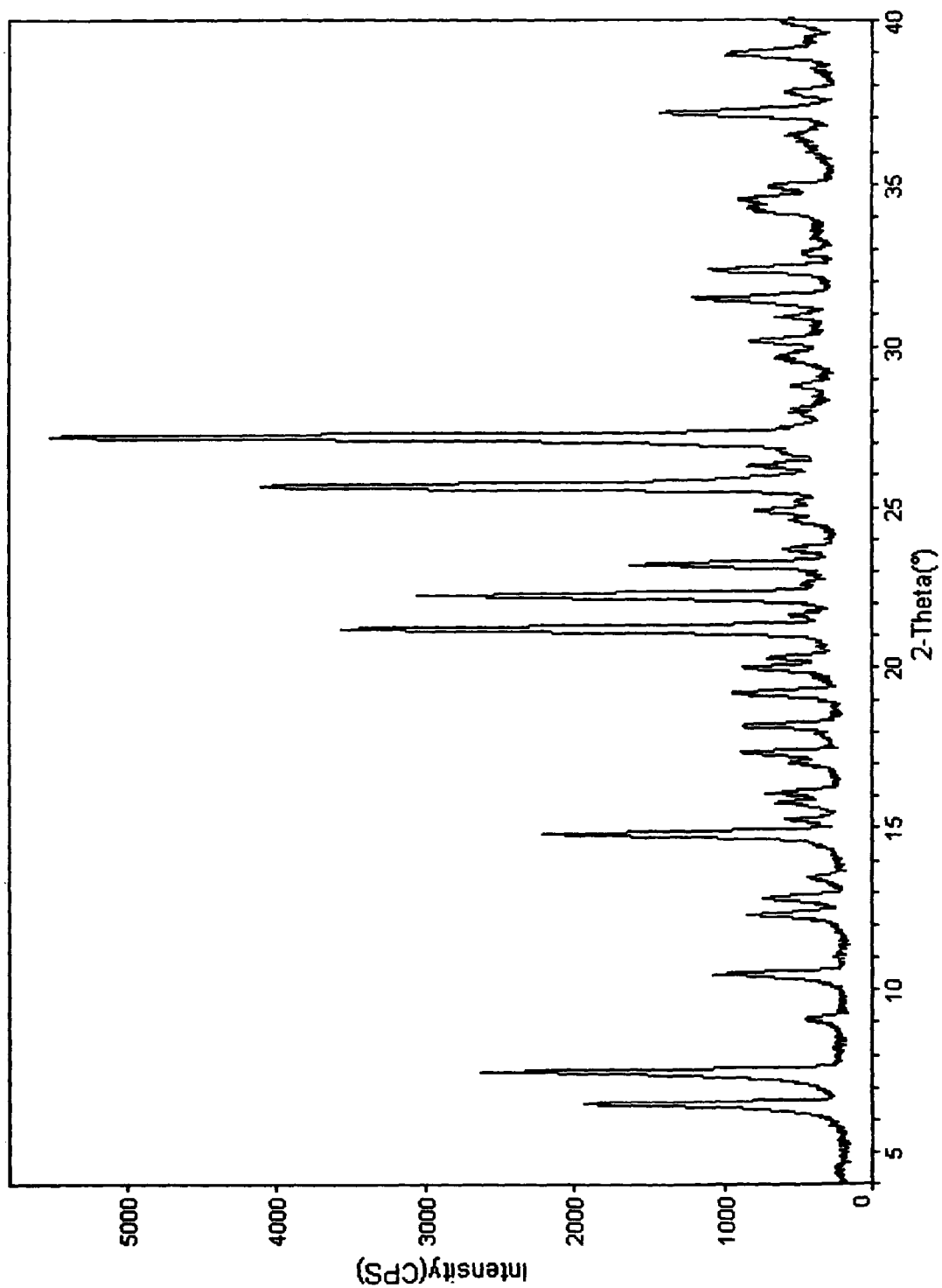
FIG. 4 presents a characteristic x-ray powder diffraction pattern of the crystalline maleate monohydrate form I salt form of the compound of Formula I [Vertical Axis: Intensity CPS, counts (square root)); Horizontal Axis: Two Theta (degrees)].

Of the peaks appearing in the spectrum shown in FIG. 4, Table VII, below lists the 12 most characteristic peaks of the X-ray Powder Diffraction spectrum, expressed in diffraction angle expressed in degrees 2 theta (°2 θ), the corresponding "d" spacing in angstroms (A), and relative intensities of the signal ("RI") in the following notation: S=strong, M=medium, W=weak; V'=Very and D=diffuse:

TABLE VII

| Diffraction Angle (°2 θ ±0.2) | d spacing (A, ±0.04) | relative intensity |
| --- | --- | --- |
| 6.5 | 13.59 | S |
| 7.5 | 11.78 | VS |
| 10.4 | 8.50 | W |
| 12.3 | 7.19 | W |
| 12.8 | 6.91 | W |
| 14.8 | 5.98 | S |
| 19.2 | 4.62 | W |
| 21.2 | 4.19 | VS |
| 22.2 | 4.00 | VS |
| 23.2 | 3.83 | M |
| 25.6 | 3.48 | VS |
| 27.2 | 3.28 | VS |

Of the peaks characteristic of the maleate monohydrate Form I salt of the compound of Formula I shown in Table VII, the eight most characteristic peaks are those appearing at diffraction angles (in °2 θ equal to 6.5, 7.5, 14.8, 21.2, 22.2, 25.6, 27.2, and 31.5, and the four most characteristic peaks are those appearing at diffraction angles (in °2 θ) equal to 6.5, 7.5, 21.2, and 27.2.

Figure 5A:
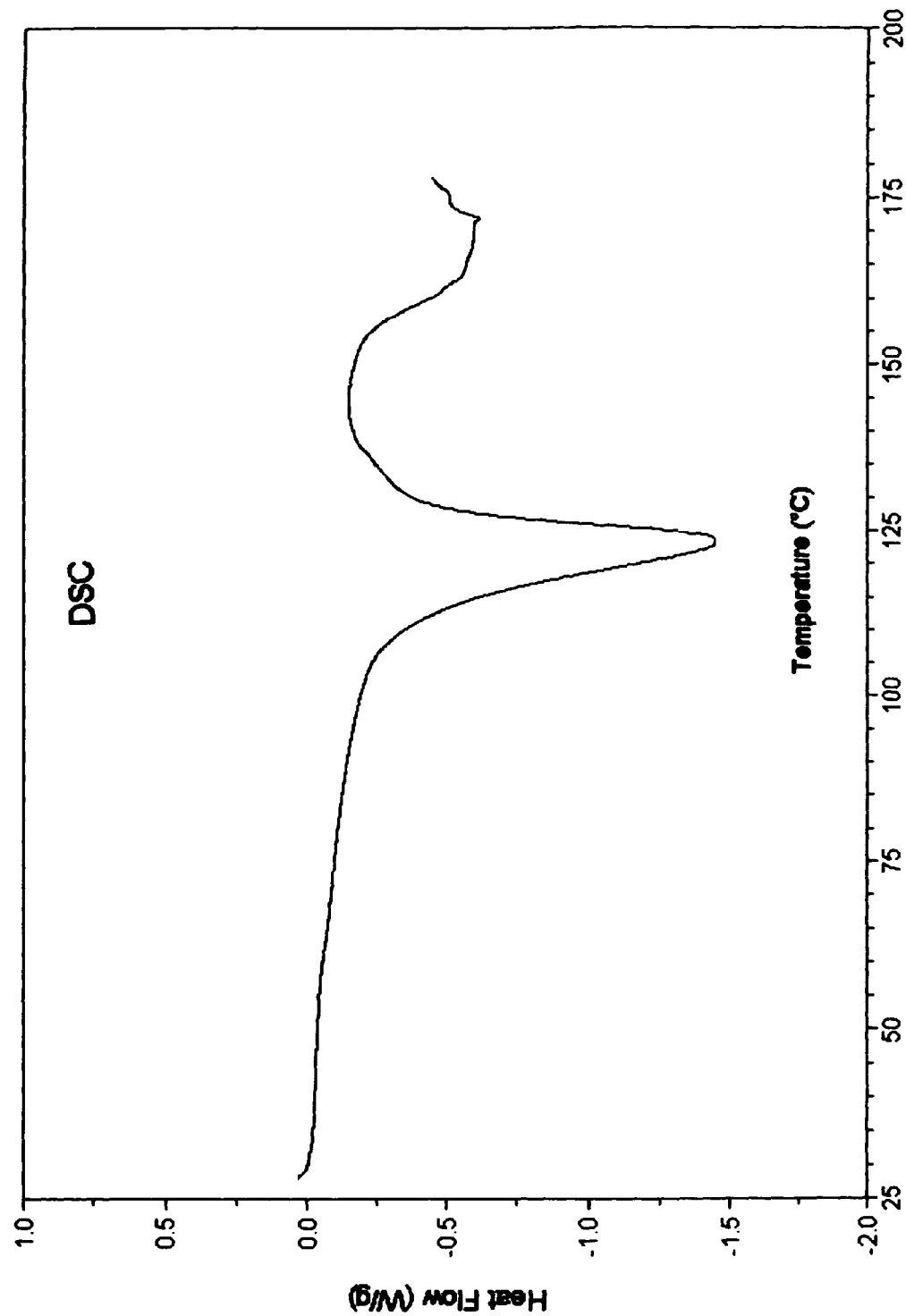
FIG. 5a presents a characteristic differential scanning calorimetry (DSC) thermogram of the crystalline maleate monohydrate form I salt form of the compound of Formula I obtained at a heating rate of 10° C./minute, [Vertical Axis; Heat Flow in cal/sec/g; Horizontal Axis: Temperature in degrees centigrade].
Figure 6:
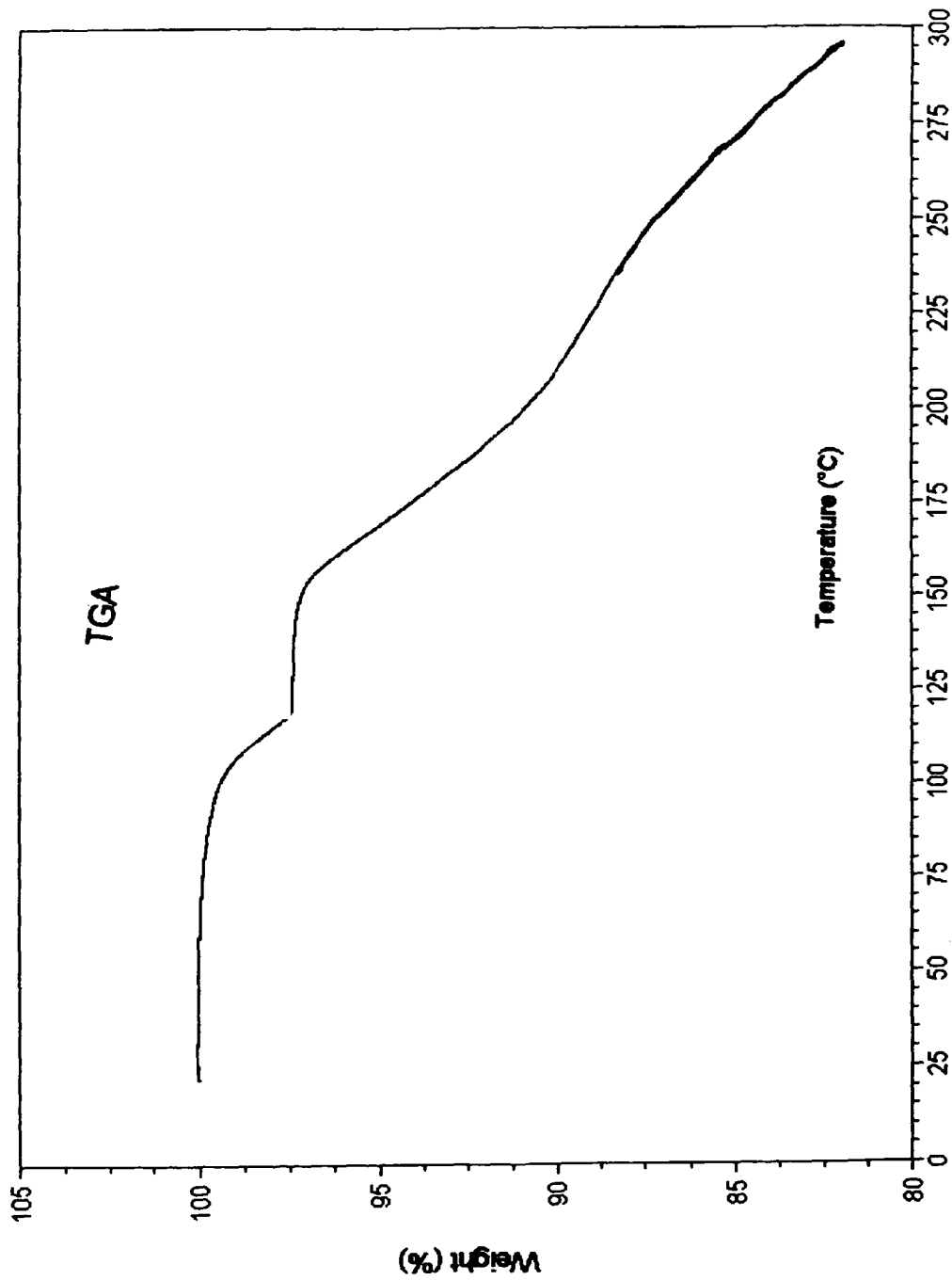
FIG. 6 presents a characteristic thermogravimetric analysis (TGA) of the crystalline maleate monohydrate form I salt form of the compound of Formula I, [horizontal axis; temperature, ° C., vertical axis; percent weight loss in sample].

FIG. 5a illustrates a DSC thermogram of the maleate monohydrate Form I salt Form of the compound of Formula I, obtained at a heating rate of 10° C./min. in accordance with the above-described procedures, and FIG. 6 illustrates thermogravimetric analysis of the maleate monohydrate Form I salt form, obtained in accordance with the above-described procedures. The DSC analysis indicates that the monohydrate Form 1 is dehydrated over the range of 100° C. to 140° C. This TGA analysis confirms that the material is a monohydrate by the sharp 2.7% weight loss observed at 125° C., with slow decomposition at temperatures over about 150° C. The weight loss observed in the TGA and 125° C. corresponds to a theoretical water content of 2.7 wt. % for the monohydrate.

Figure 5B:
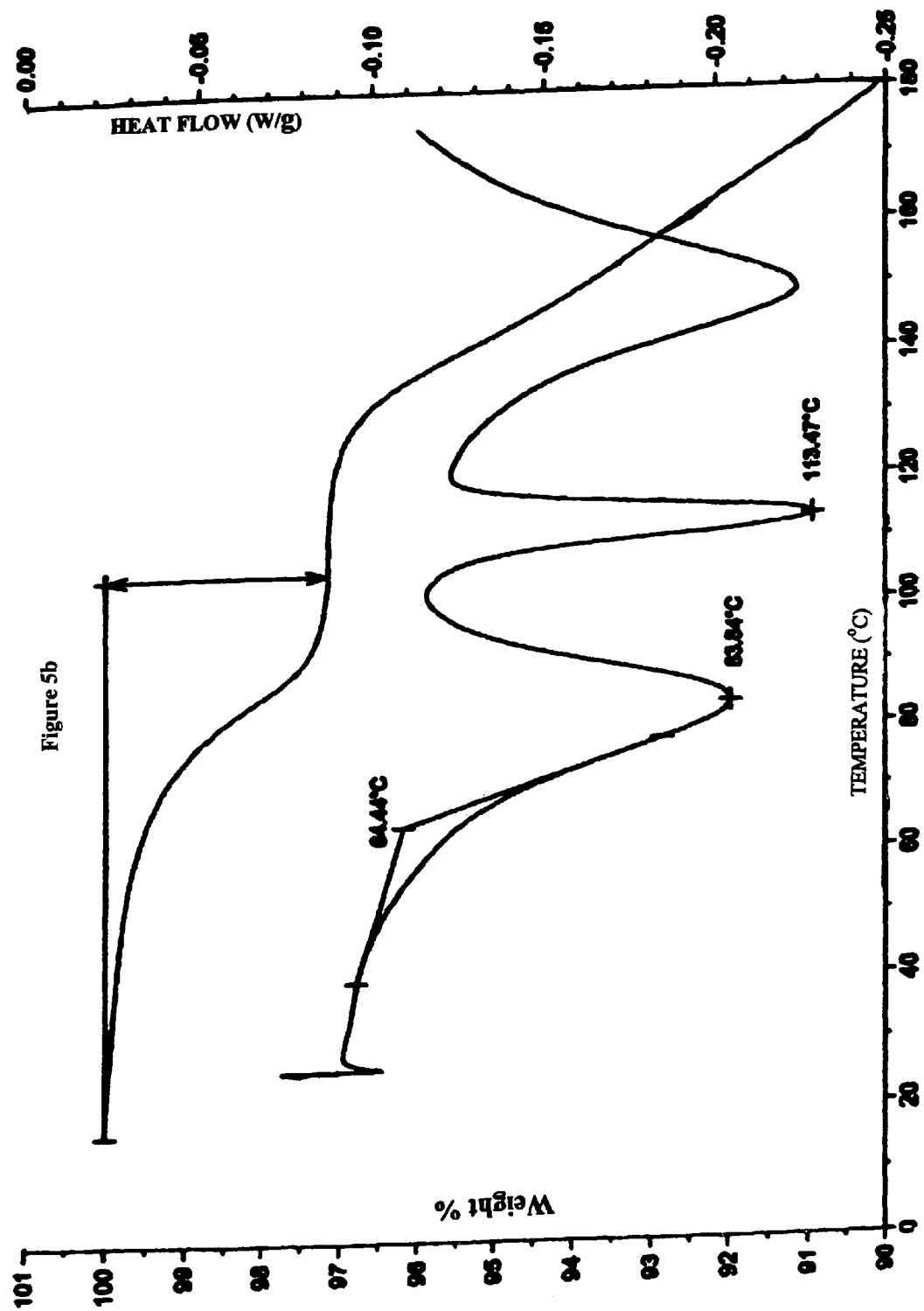
FIG. 5b presents a characteristic differential scanning calorimetry (DSC) thermogram of the crystalline maleate monohydrate form I salt form of the compound of Formula I obtained at a heating rate of 2° C./minute, [Vertical Axis; Heat Flow in cal/sec/g; Horizontal Axis: Temperature in degrees centigrade]

The DSC thermograph shown in FIG. 5b was obtained at a 2° C. heating rate on a sample of crystalline maleate monohydrate form I salt of the compound of Formula I, and appears overlayed with the TGA thermogram of FIG. 6. As can be seen there are two distinct regions in the DSC, a first endotherm peaking at about 84° C. corresponding to dehydration of the monohydrate (which is confirmed by the TGA) and a second region peaking at 113.5° C., corresponding to decomposition of the crystalline phase. It was determined that heating a sample of the crystalline maleate monohydrate form I salt at a temperature above its dehydration temperature but below its decomposition temperature yields a dehydrated structure which, when cooled and exposed to water vapor, reverts to its initial monohydrate structure.

The crystalline maleate monohydrate Form I salt of the compound of Formula I was investigated for photo stability in accordance with ICH-photostability conditions. Samples of the salt exposed to one cycle of ICH photostability conditions did not show any significant degradation. Samples of the crystalline maleate monohydrate Form I salt of the compound of Formula I were investigated also for chemical stability with the results shown below in Table VIII.

TABLE VIII

| Conditions | Exposure Time | % Recovered of initial compound |
| --- | --- | --- |
| −20° C. | 1 month | 99.5 |
| 40° C., 75% relative humidity | 1 month | 99.4 |
| 50° C. | 1 month | 99.7 |

The data in Table VIII indicate that the crystalline maleate monohydrate salt form I did not show any decomposition under the test conditions. The maleate monohydrate Form I salt form of the compound of Formula I was also investigated under ambient conditions at relative humidity from 5% to 95% with the following results: (a) 5% RH, no measurable moisture uptake; (b) 35% RH, 0.06% uptake; (c) 55% RH, 0.12% uptake; (d) 75% RH, 0.18% uptake; and (e) 95% RH, 0.20% uptake. Accordingly, the salt form shows superior moisture stability under ordinary ambient conditions.

Preparation of Maleate Monohydrate Form 2 Salt Form

A 5.0 g (9.57 mmol) aliquot of the compound of Formula I (free base form) was suspended in a mixture of 10 ml acetonitrile and 25 ml of t-butylmethylether (TBME). The suspension was heated to 50° C. and 1.4 g maleic acid (1.3 eq.), resulting in dissolution of the suspend material. The solution was cooled to ambient temperature (about 25° C.) over a 30 minute period producing a white precipitate. The solids were obtained (4.6 g) by filtration. Calculated yield was 76% based on starting free base.

The dried crystals of maleate monohydrate Form 2 salt were analyzed by X-ray powder diffraction spectroscopy (FIG. 7), differential scanning calorimetry (FIG. 8) and thermogravimetric analysis (FIG. 9) according the above-described procedures.

Figure 7:
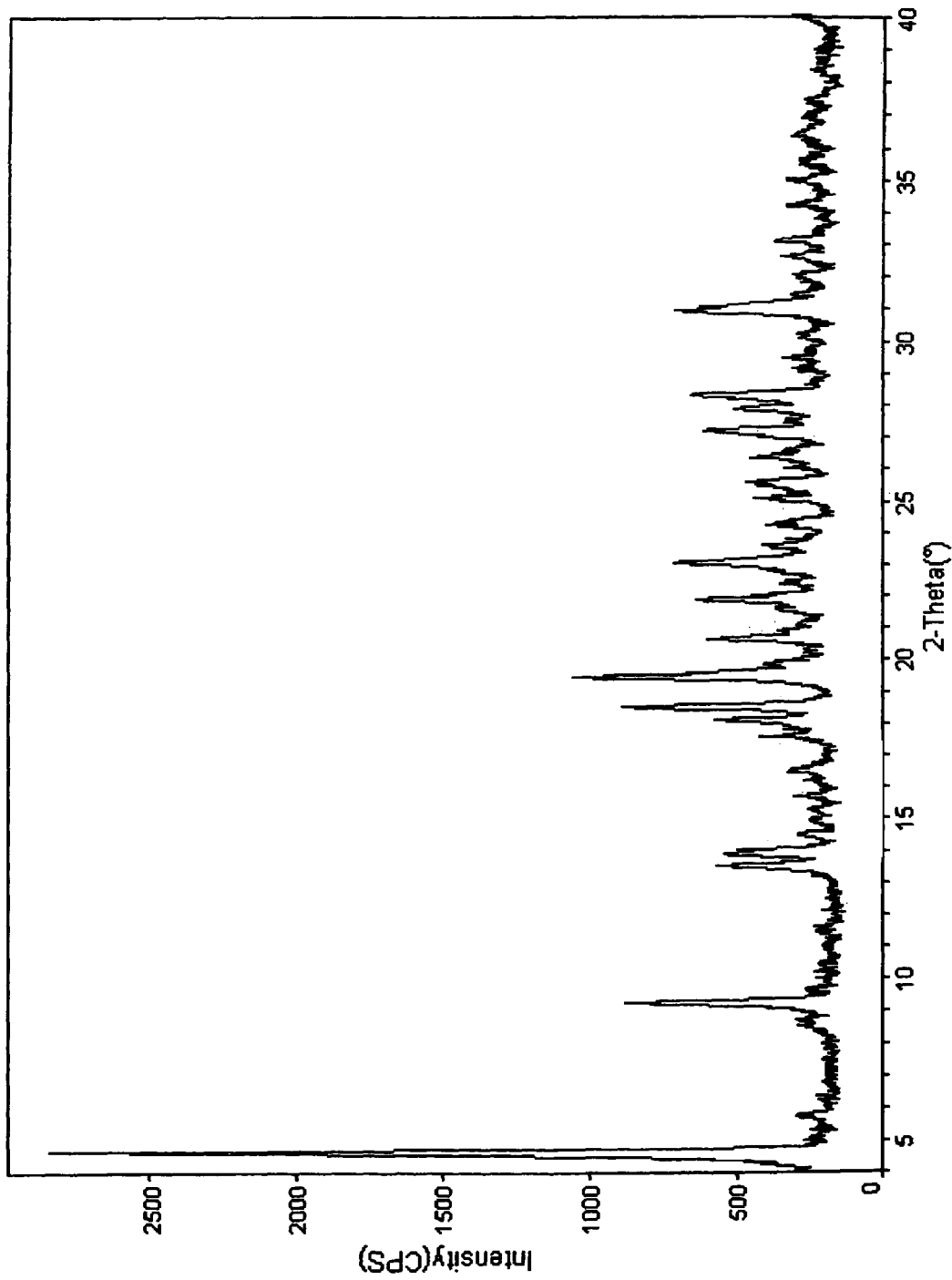
FIG. 7 presents a characteristic x-ray powder diffraction pattern of the crystalline maleate monohydrate form 2 salt form of the compound of Formula I [Vertical Axis: Intensity CPS, counts (square root)); Horizontal Axis: Two Theta (degrees)].

The X-ray powder diffraction spectrum obtained on a sample of the maleate monohydrate Form 2 salt appearing in FIG. 7 exhibits absorption peaks at the following diffraction angles having the intensity shown in Table IX:

TABLE IX

| Peak position (2-Theta) | Intensity (CPS) |
| --- | --- |
| 4.7 | 2615 |
| 5.8 | 113 |
| 8.7 | 101 |
| 9.3 | 675 |
| 13.5 | 393 |
| 13.9 | 364 |
| 14.5 | 98 |
| 15.3 | 69 |
| 15.7 | 120 |
| 16.4 | 141 |
| 18.1 | 389 |
| 18.5 | 661 |
| 19.4 | 848 |
| 19.9 | 167 |
| 20.6 | 369 |
| 21.5 | 125 |
| 21.9 | 396 |
| 22.4 | 97 |
| 23.0 | 477 |
| 23.6 | 186 |
| 24.2 | 193 |
| 25.0 | 239 |
| 25.5 | 259 |
| 26.3 | 228 |
| 27.2 | 360 |
| 27.9 | 284 |
| 28.3 | 426 |
| 29.2 | 107 |
| 29.5 | 138 |
| 30.2 | 83 |
| 31.0 | 506 |
| 31.4 | 113 |
| 32.0 | 90 |
| 32.6 | 165 |
| 33.0 | 193 |
| 34.2 | 135 |
| 35.0 | 140 |
| 35.5 | 88 |
| 36.4 | 91 |
| 38.4 | 67 |

Of the peaks appearing in the spectrum shown in FIG. 7, Table X, below lists the 12 most characteristic peaks of the X-ray Powder Diffraction spectrum, expressed in diffraction angle expressed in degrees 2 theta (°2 θ), the corresponding "d" spacing in angstroms (A), and relative intensities of the signal ("RI") in the following notation: S=strong, M=medium, W=weak; V=Very and D=diffuse:

TABLE X

| Diffraction Angle (°2 θ .± 0.2) | d spacing (A, ±0.04) | relative intensity |
| --- | --- | --- |
| 4.7 | 18.78 | VS |
| 9.3 | 9.50 | M |
| 13.5 | 6.55 | M |
| 13.9 | 6.37 | M |

TABLE X-continued

| Diffraction Angle (°2 θ .± 0.2) | d spacing (A, ±0.04) | relative intensity |
| --- | --- | --- |
| 16.4 | 5.40 | W |
| 18.1 | 4.90 | M |
| 18.5 | 4.79 | M |
| 19.4 | 4.57 | S |
| 20.6 | 4.31 | M |
| 21.9 | 4.05 | M |
| 23.0 | 3.86 | M |
| 31.0 | 2.88 | M |

Of the peaks characteristic of the maleate monohydrate Form 2 salt of the compound of Formula I shown in Table X, the eight most characteristic peaks are those appearing at diffraction angles (in °2 θ equal to 4.7, 9.3, 13.9, 18.1, 18.5, 19.4, 20.6 and 23.0, and the four most characteristic peaks are those appearing at diffraction angles (in °2 θ) equal to 4.7, 9.3, 18.5 and 19.4.

Figure 8:
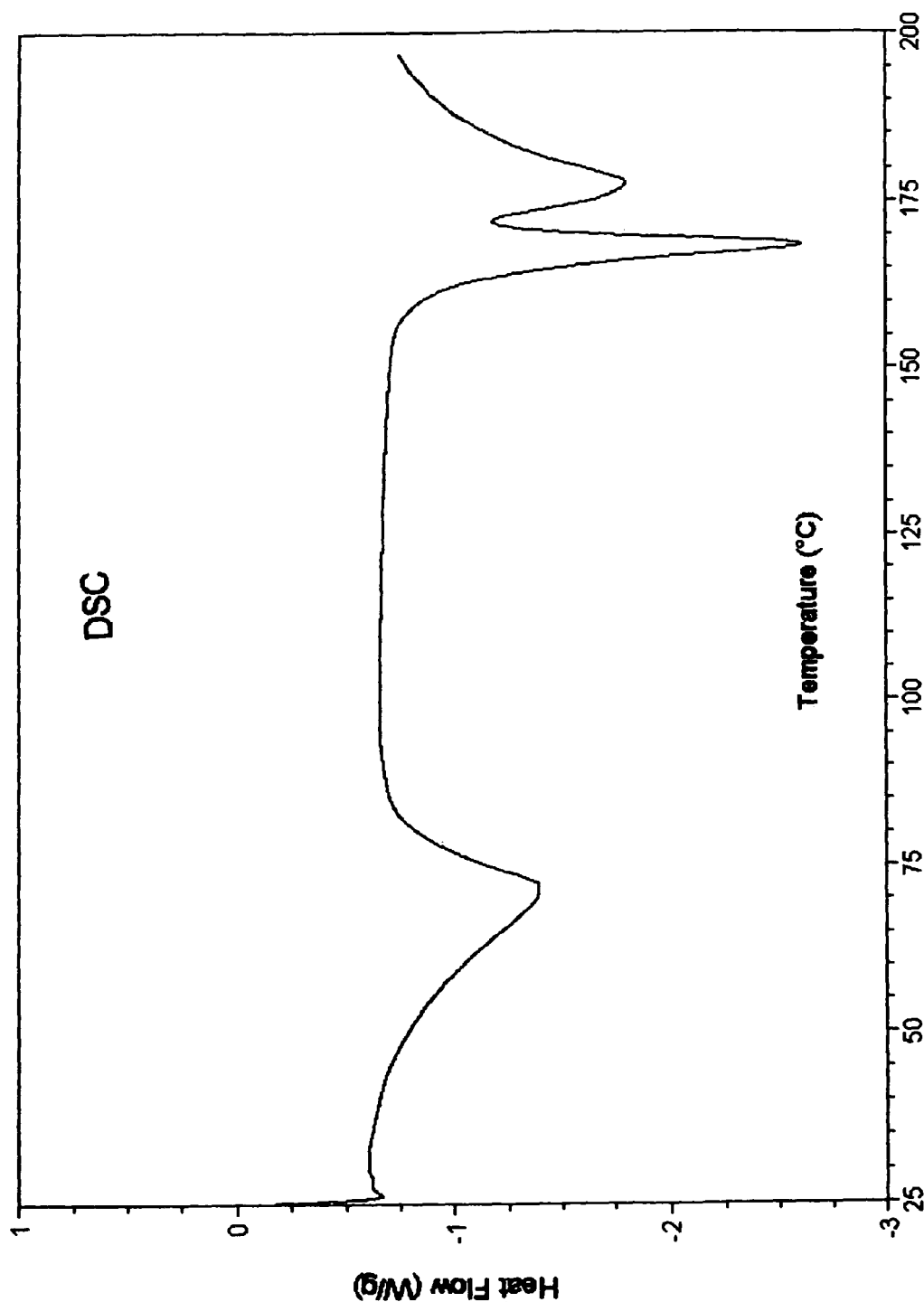
FIG. 8 presents a characteristic differential scanning calorimetry (DSC) thermogram of the crystalline maleate monohydrate form 2 salt form of the compound of Formula II, [Vertical Axis; Heat Flow in cal/sec/g; Horizontal Axis: Temperature in degrees centigrade].
Figure 9:
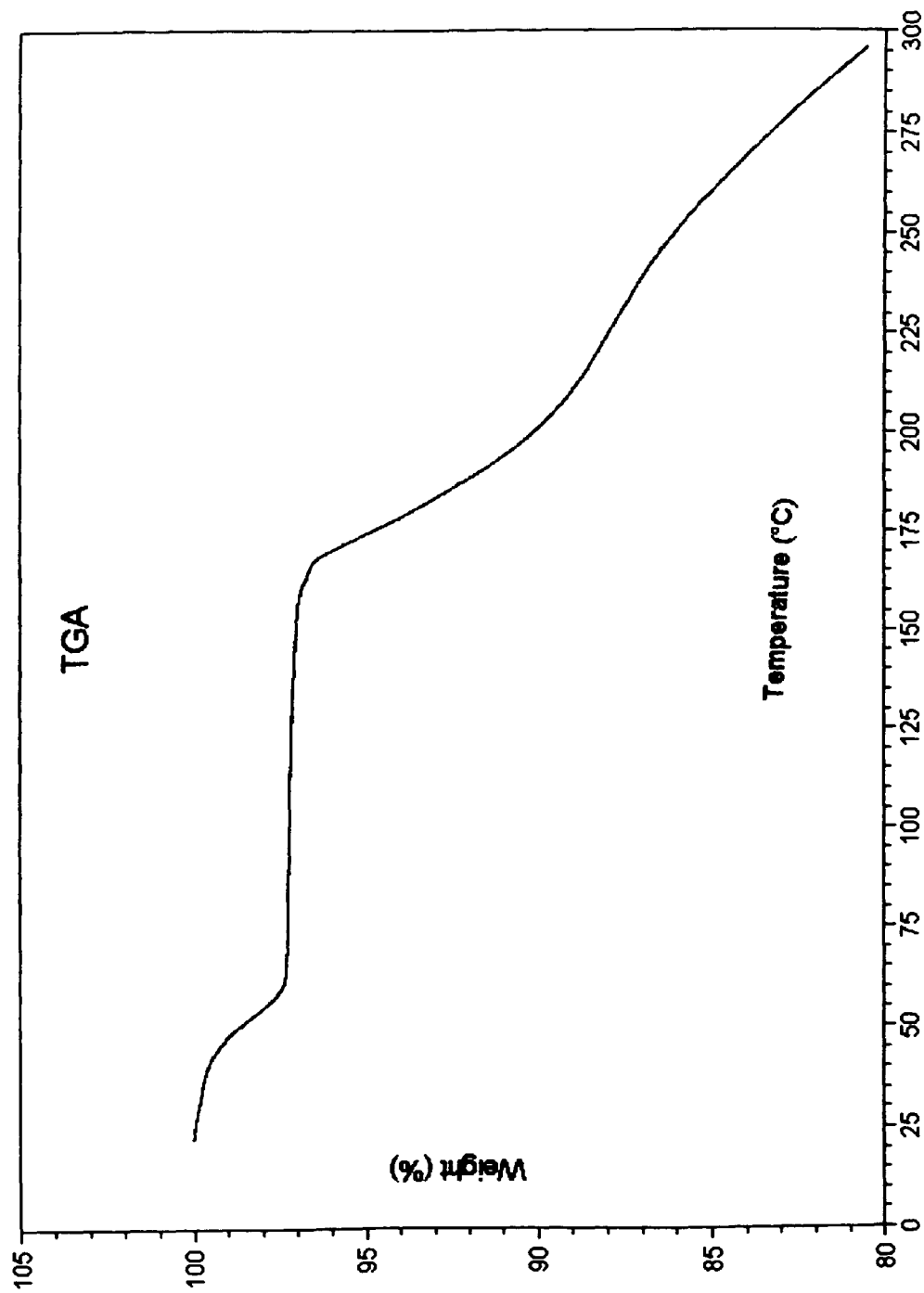
FIG. 9 presents a characteristic thermogravimetric analysis (TGA) of the crystalline maleate monohydrate form 2 salt form of the compound of Formula I, [horizontal axis; temperature, ° C., vertical axis; percent weight loss in sample].
Figure 10:
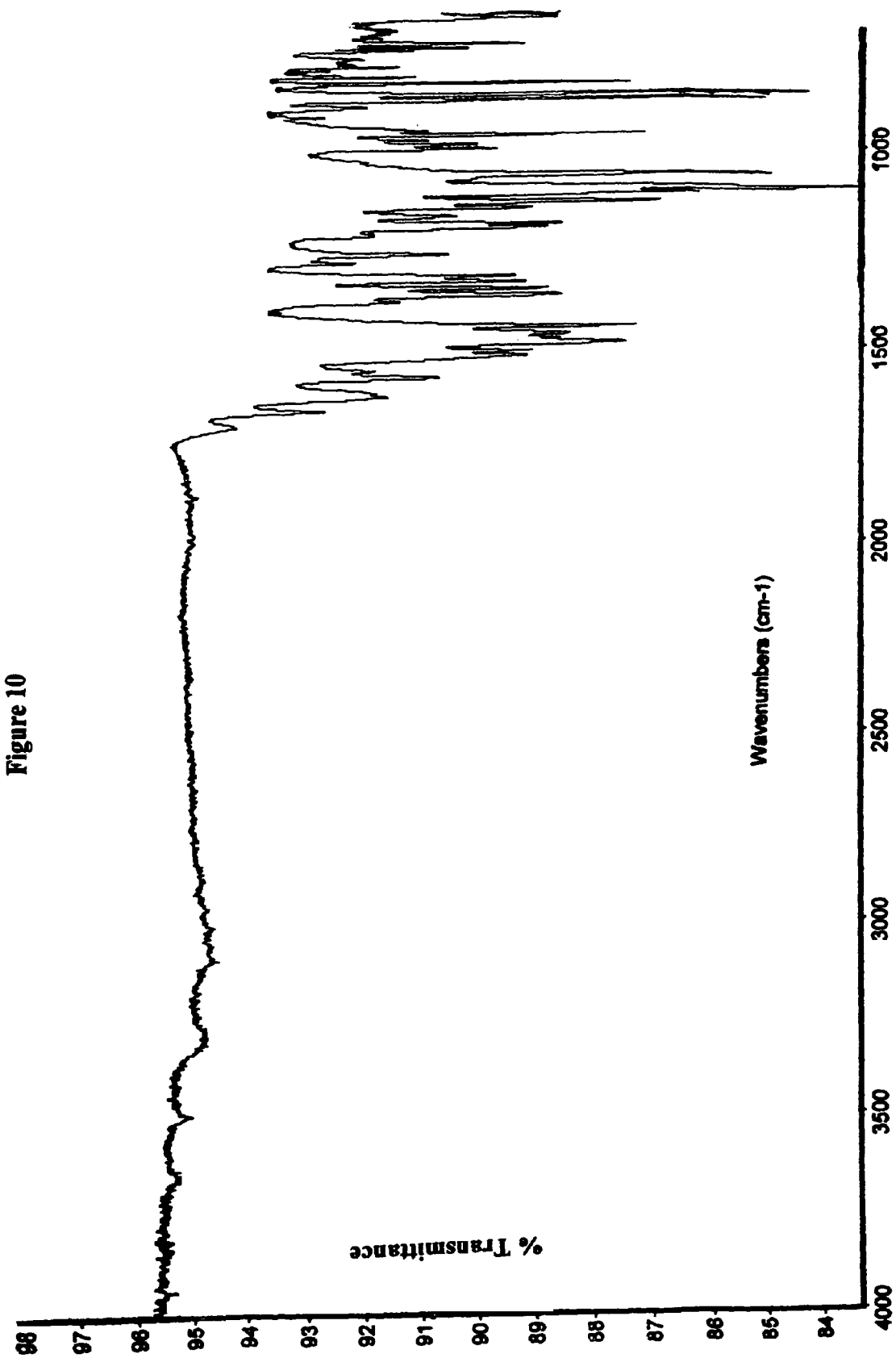
FIG. 10 presents a characteristic infrared spectrum pattern of the crystalline maleate monohydrate form I salt form of the compound of Formula I [Vertical Axis: % transmittance; Horizontal Axis: wave numbers in cm$^{-1}$].

FIG. 8 illustrates a DSC thermogram of the maleate monohydrate Form 2 salt Form of the compound of Formula I, obtained in accordance with the above-described procedures, and FIG. 9 illustrates thermogravimetric analysis of the maleate monohydrate Form 2 salt form. The DSC analysis indicates that the monohydrate Form 2 is dehydrated over the range of 40° C. to 85° C. In this temperature range the TGA analysis indicates a weight loss of about 2.7%, which is consistent with the loss of one eq. of water/molecule of the salt, confirming that the structure is the monohydrate. The TGA further indicates slow decomposition at temperatures over about 150° C.

Preparation of Fumarate Salt Form of the Compound of Formula I

A 6.0 g (11.5 mmol) aliquot of the compound of Formula I (free base form) was suspended in 50 ml of acetonitrile. The suspension was heated to 60° C. and 1.4 g (12.1 mmol, 1.05 eq) of fumaric acid was added. The mixture was heated to 80° C. providing a solution. The solution was cooled to room temperature (about 25° C.) over a 2 hour period, precipitating solids. The solids were collected by vacuum filtration and dried in a vacuum oven for 2 hours at 50° C. yielding 6.8 g of crystalline needles (calculated yield, 92.7% based on starting free base).

The dried crystals of the fumarate salt form of the compound of Formula I thus prepared were analyzed by X-ray powder diffraction spectroscopy (FIG. 12), differential scanning calorimetry (FIG. 13) and thermogravimetric analysis (FIG. 14) according the above-described procedures.

Figure 12:
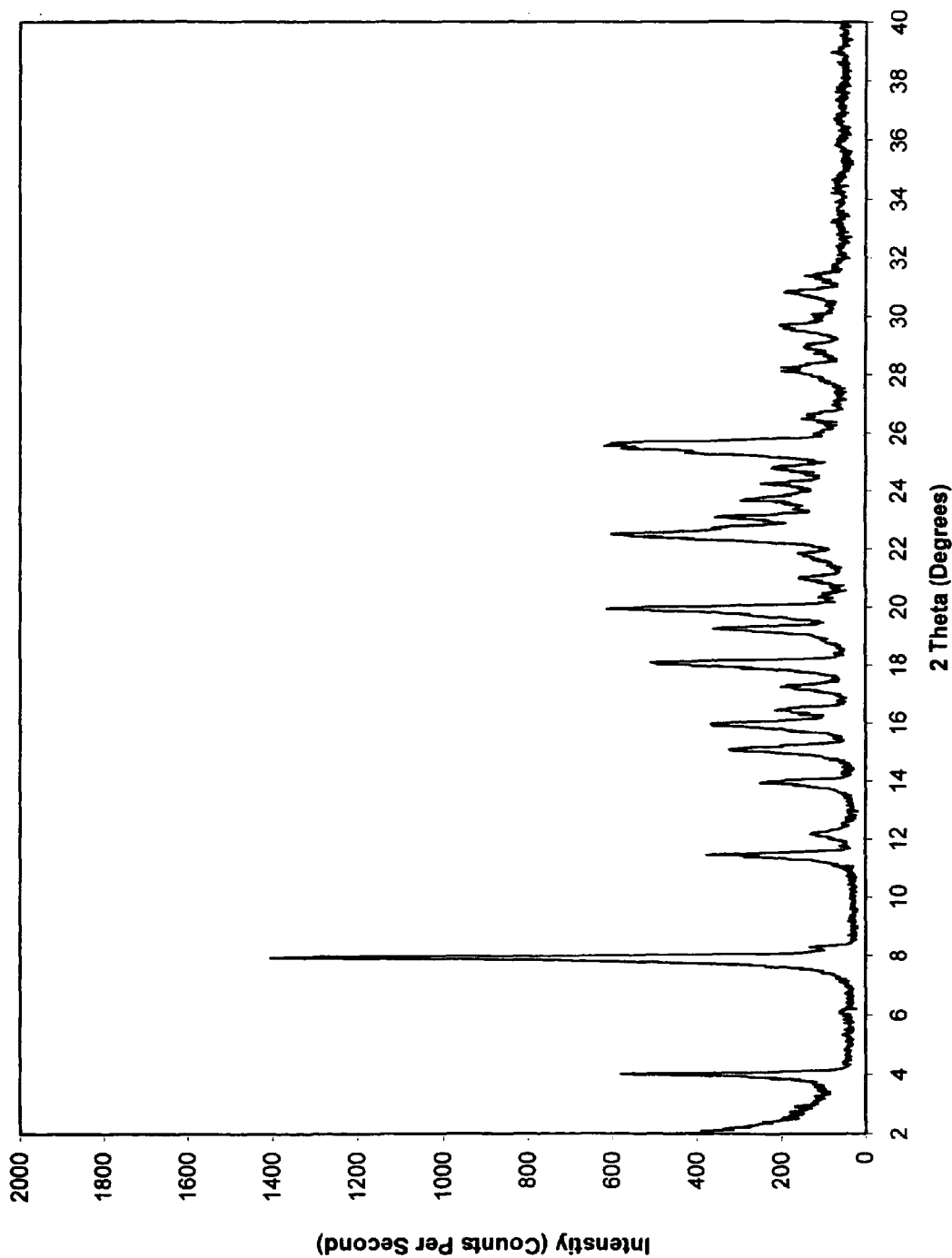
FIG. 12 presents a characteristic x-ray powder diffraction pattern of the crystalline fumarate salt form of the compound of Formula I [Vertical Axis: Intensity CPS, counts (square root)); Horizontal Axis: Two Theta (degrees)].

The X-ray powder diffraction spectrum obtained on a sample of the above-prepared crystalline fumarate salt form appearing in FIG. 12 exhibits absorption peaks at the following diffraction angles having the intensity shown in Table XIX:

TABLE XIX

| Peak position (2-Theta) | Intensity (CPS) |
| --- | --- |
| 3.8 | 122 |
| 4.0 | 493 |
| 7.69 | 157 |
| 7.8 | 452 |
| 8.0 | 1470 |
| 11.5 | 333 |
| 13.9 | 225 |
| 15.1 | 303 |
| 15.9 | 343 |

TABLE XIX-continued

| Peak position (2-Theta) | Intensity (CPS) |
| --- | --- |
| 16.4 | 162 |
| 17.2 | 142 |
| 17.9 | 217 |
| 18.0 | 512 |
| 19.2 | 322 |
| 19.6 | 167 |
| 19.9 | 608 |
| 21.0 | 112 |
| 22.5 | 552 |
| 22.7 | 252 |
| 23.0 | 272 |
| 23.7 | 190 |
| 24.2 | 138 |
| 24.8 | 118 |
| 25.3 | 338 |
| 25.5 | 543 |
| 25.6 | 567 |
| 28.1 | 140 |
| 28.2 | 113 |
| 29.6 | 125 |
| 29.7 | 148 |
| 30.8 | 122 |

Of the peaks appearing in the spectrum shown in FIG. 12, Table XI below lists the 12 most characteristic absorption peaks at diffraction angles and relative intensity shown in Table XI, below. Table XI lists also the calculated lattice spacing determined from the x-ray data in FIG. 12. In Table XI diffraction angle is expressed in degrees 2 theta (°2 θ), the corresponding "d" spacing in angstroms (A), and relative intensities of the signal ("RI") in the following notation: S=strong, M=medium, W=weak; V=Very and D=diffuse:

TABLE XI

| Diffraction Angle (°2 θ .± 0.2) | d spacing (A, ±0.04) | relative intensity |
| --- | --- | --- |
| 4.0 | 22.07 | M |
| 7.8 | 11.32 | M |
| 8.0 | 11.04 | S |
| 11.5 | 7.69 | W |
| 15.9 | 5.57 | W |
| 18.0 | 4.92 | M |
| 19.2 | 4.62 | W |
| 19.9 | 4.46 | M |
| 22.5 | 3.95 | M |
| 25.3 | 3.52 | W |
| 25.5 | 3.49 | M |
| 25.6 | 3.48 | M |

Of the peaks characteristic of the crystalline fumarate salt form of the compound of Formula I shown in Table XI, the eight most characteristic peaks are those appearing at diffraction angles (in °2 θ equal to 4.0, 7.8, 8.0, 18.0, 19.9, 22.5, 25.5, and 25.6, and the four most characteristic peaks are those appearing at diffraction angles (in °2 θ) equal to 8.0, 19.9, 22.5 and 25.6.

Figure 13:
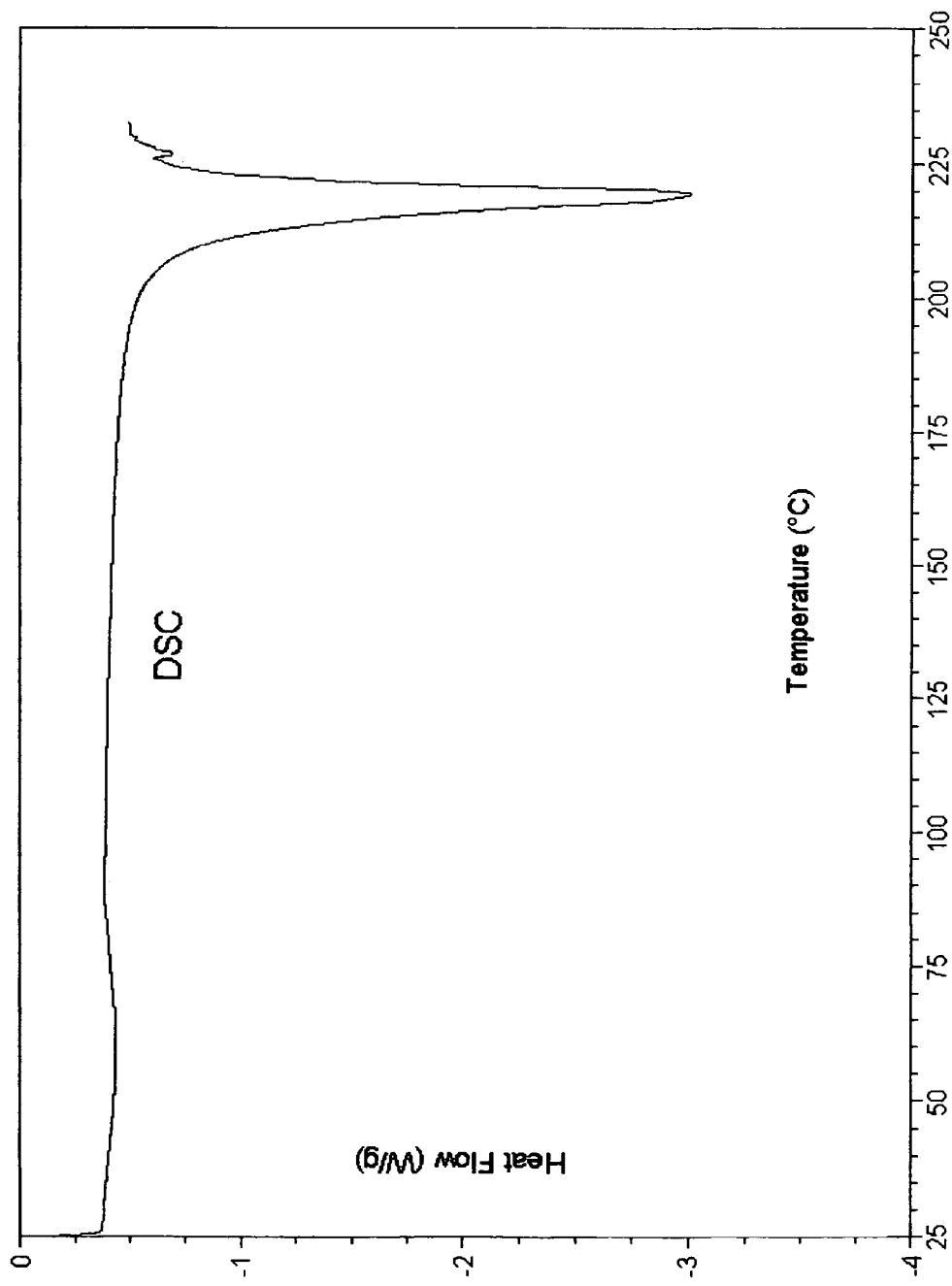
FIG. 13 presents a characteristic differential scanning calorimetry (DSC) thermogram of the crystalline fumarate salt form of the compound of Formula II, [Vertical Axis; Heat Flow in cal/sec/g; Horizontal Axis: Temperature in degrees centigrade].
Figure 14:
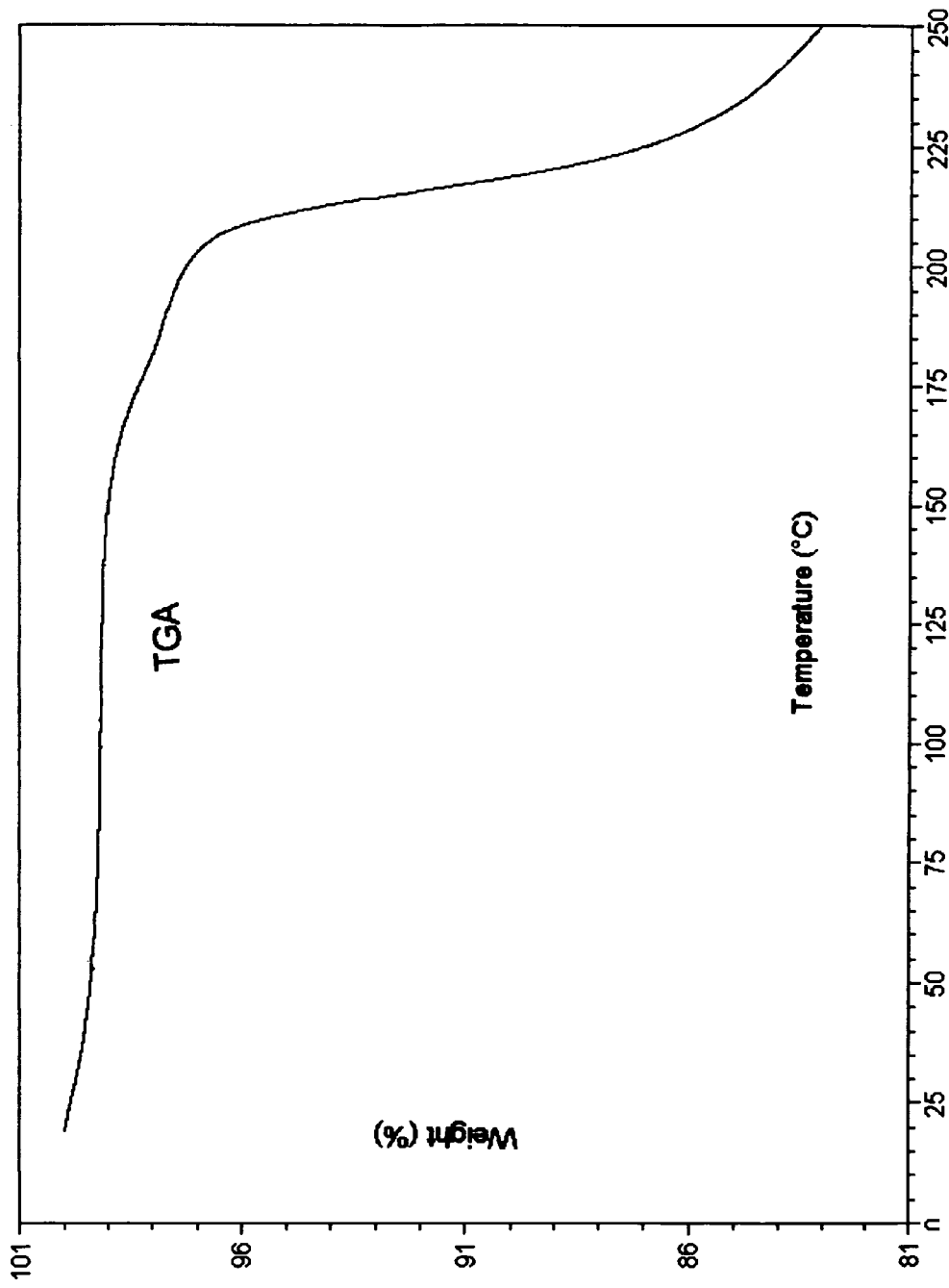
FIG. 14 presents a characteristic thermogravimetric analysis (TGA) of the crystalline fumarate salt form of the compound of Formula I, [horizontal axis; temperature, ° C., vertical axis; percent weight loss in sample].

FIG. 13 illustrates a DSC thermogram of the fumarate salt of the compound of Formula I, obtained in accordance with the above-described procedures, and FIG. 14 illustrates thermogravimetric analysis of the fumarate salt. The DSC analysis indicates that the fumarate salt is stable over the range of 25° C. to 200° C. with a sharp melting point at about 215° C. The TGA analysis confirms that the material is not a solvate, displaying no significant weight loss until the melting point indicated by DSC.

The crystalline fumarate salt form prepared above was investigated under ambient conditions at relative humidity from 5% to 95% with the following results: (a) 5% RH, no measurable moisture uptake; (b) 35% RH, 0.21% uptake; (c) 55% RH, 0.40% uptake; (d) 75% RH, 0.64% uptake; and (e) 95% RH, 0.80% uptake. Accordingly, the salt form shows superior moisture stability under ordinary ambient conditions.

Preparation of Tosylate Anhydride

Form I Salt Form of the Compound of Formula I

An 11.0 g (21.1 mmol) aliquot of the compound of Formula I (free base form) was suspended in 130 ml of acetonitrile. The suspension was heated to 60° C. and 4.5 g (23.7 mmol, 1.19 eq.) of toluenesulfonic acid was added. The mixture was further heated to 70° C. and 80 ml of t-butyl methylether was added over 20 minutes using an additional funnel. The resulting solution was cooled to ambient temperature (about 25° C.) over a 2 hour period precipitating white needles. The solids were collected by filtration (13.7 g). Calculated yield was 93.7% based on starting free base.

The dried crystals of Tosylate Anhydride Form I Salt were analyzed by X-ray powder diffraction spectroscopy (FIG. 15), differential scanning calorimetry (FIG. 16) and thermogravimetric analysis (FIG. 17) according the above-described procedures.

Figure 15:
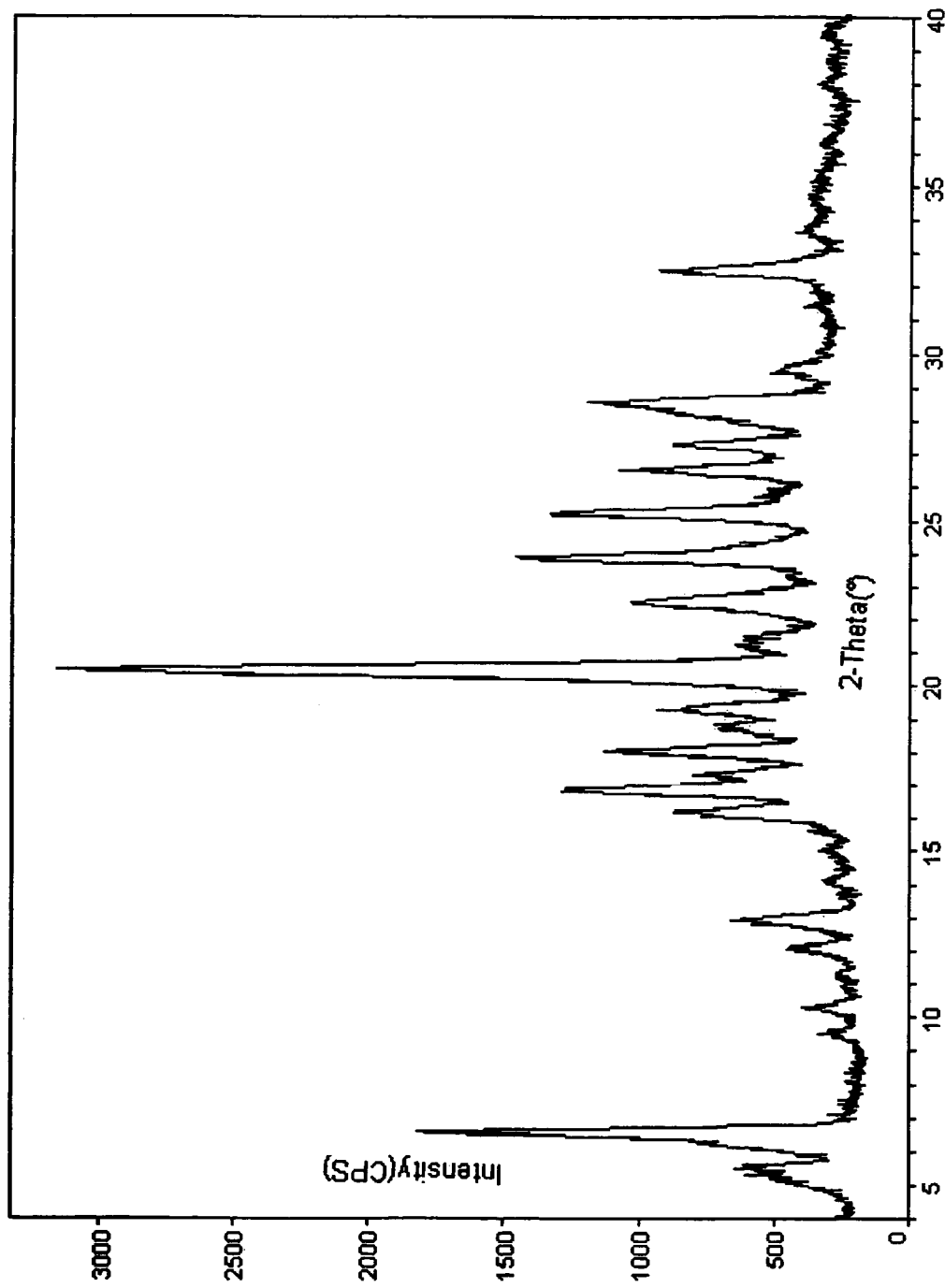
FIG. 15 presents a characteristic x-ray powder diffraction pattern of the crystalline tosylate form I salt form of the compound of Formula I [Vertical Axis: Intensity CPS, counts (square root)); Horizontal Axis: Two Theta (degrees)].

The X-ray powder diffraction spectrum obtained on a sample of the tosylate anhydrous Form 1 salt Form of the compound of Formula I appearing in FIG. 15 exhibits absorption peaks at the following diffraction angles having the intensity shown in Table XII:

TABLE XII

| Peak position (2-Theta) | Intensity (CPS) |
| --- | --- |
| 5.5 | 340 |
| 6.2 | 441 |
| 6.6 | 1557 |
| 9.5 | 139 |
| 10.3 | 190 |
| 12.1 | 214 |
| 12.9 | 418 |
| 14.1 | 89 |
| 15.0 | 97 |
| 16.2 | 641 |
| 16.8 | 862 |
| 17.3 | 342 |
| 18.0 | 678 |
| 18.7 | 243 |
| 19.3 | 478 |
| 20.5 | 2675 |
| 21.2 | 170 |
| 22.6 | 645 |
| 23.9 | 1059 |
| 25.2 | 919 |
| 26.5 | 637 |
| 27.3 | 395 |
| 28.0 | 248 |
| 28.5 | 812 |
| 29.5 | 158 |
| 32.5 | 633 |
| 33.6 | 114 |
| 37.98 | 96 |

Of the peaks appearing in the spectrum shown in FIG. 15, Table XIII, below, lists the 12 most characteristic peaks of the X-ray Powder Diffraction spectrum, with diffraction angle expressed in degrees 2 theta (°2 θ), the corresponding "d" spacing in angstroms (A), and relative intensities of the signal ("RI") in the following notation: S=strong, M=medium, W=weak; V=Very and D=diffuse:

TABLE XIII

| Diffraction Angle (°2 θ ± 0.2) | d spacing (A, ±0.04) | relative intensity |
|---|---|---|
| 5.5 | 16.05 | W |
| 6.6 | 13.38 | S |
| 10.3 | 8.58 | W |
| 12.9 | 6.86 | W |
| 16.2 | 5.47 | M |
| 16.8 | 5.27 | M |
| 18.0 | 4.92 | M |
| 20.5 | 4.33 | VS |
| 22.6 | 3.93 | M |
| 23.9 | 3.72 | S |
| 25.2 | 3.53 | M |
| 32.5 | 2.75 | M |

Of the peaks characteristic of the tosylate anhydrous Form 1 salt Form of the compound of Formula I shown in Table XIII, the eight most characteristic peaks are those appearing at diffraction angles (in °2 θ) equal to 5.5, 6.6, 12.9, 16.8, 20.5, 23.9, 25.2, and 28.5, and the four most characteristic peaks are those appearing at diffraction angles (in °2 θ) equal to 6.6, 16.8, 20.5 and 23.9.

Figure 16:
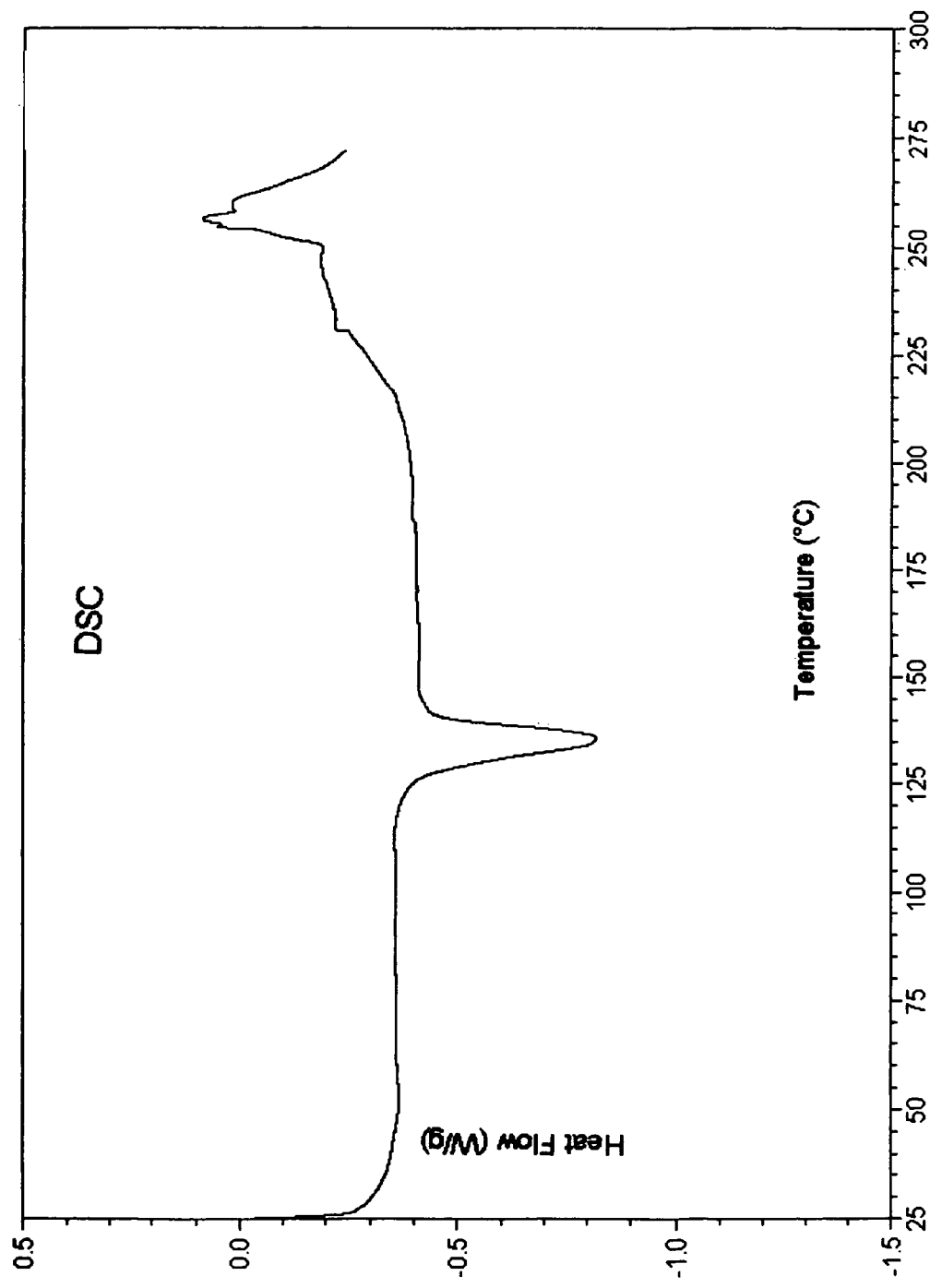
FIG. 16 presents a characteristic differential scanning calorimetry (DSC) thermogram of the crystalline tosylate form I salt form of the compound of Formula I, [Vertical Axis; Heat Flow in cal/sec/g; Horizontal Axis: Temperature in degrees centigrade].
Figure 17:
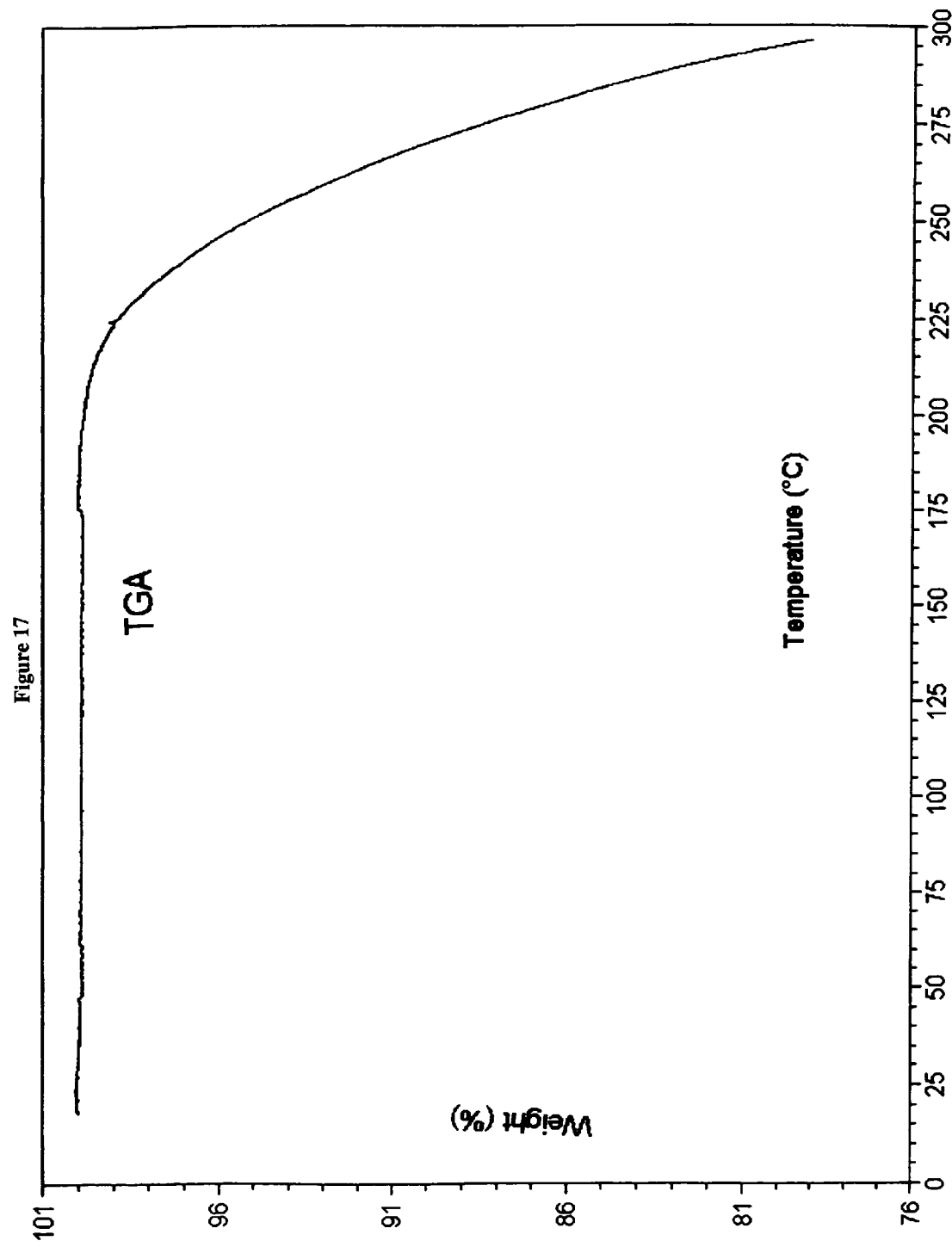
FIG. 17 presents a characteristic thermogravimetric analysis (TGA) of the crystalline tosylate form I salt form of the compound of Formula I, [horizontal axis; temperature, ° C., vertical axis; percent weight loss in sample].

FIG. 16 illustrates a DSC thermogram of the tosylate anhydrous Form 1 salt Form of the compound of Formula I, obtained in accordance with the above-described procedures, and FIG. 17 illustrates thermogravimetric analysis of the tosylate anhydrous Form 1 salt. This thermal analysis is consistent with the tosylate anhydrous Form 1 salt being an unsolvated salt form and having a melting point of 135° C.
Preparation of Tosylate Hydrate Form I Salt Form of the Compound of Formula I An aliquot (1.5 g, 2.2 mmol) of the tosylate anhydrous form 1 salt form of the compound of Formula I prepared above was combined with 9.0 mL of water in a sealed container for 3 days producing a scum-like material. The scum-like material was collected, broken apart, and combined with an additional 15 mL of water, producing a slurry. The slurry was shaken at 25° C. and 350 RPM for six days producing a wet cake. An additional 45 mL of water was added to the wet cake, producing a slurry, which was shaken at 25° C. and 350 RPM for five days. After the shaking period had ended the resulting solids were collected by vacuum filtration and dried under vacuum at room temperature overnight, providing the tosylate hydrate Form I salt form of the compound of Formula I.

The dried crystals of tosylate hydrate Form I Salt were analyzed by X-ray powder diffraction spectroscopy (FIG. 18), differential scanning calorimetry (FIG. 19) and thermogravimetric analysis (FIG. 20) according the above-described procedures.

Figure 18:
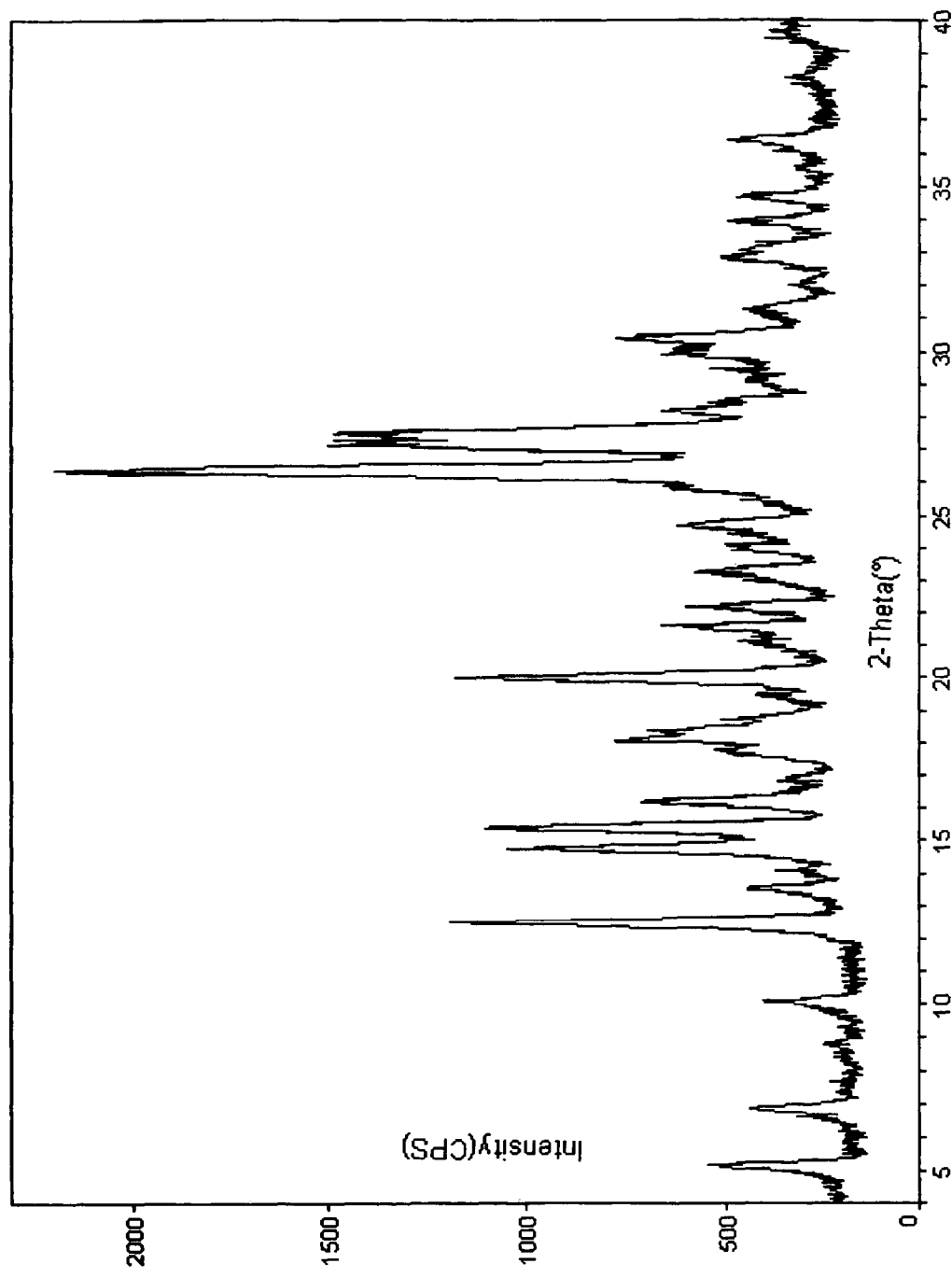
FIG. 18 presents a characteristic x-ray powder diffraction pattern of the crystalline tosylate hydrate form I salt form of the compound of Formula I [Vertical Axis: Intensity CPS, counts (square root)); Horizontal Axis: Two Theta (degrees)].

The X-ray powder diffraction spectrum obtained on a sample of the tosylate hydrate form I salt form of the compound of Formula I appearing in FIG. 18 exhibits absorption peaks at the following diffraction angles having the intensity shown in Table XIV:

TABLE XIV

| Peak position (2-Theta) | Intensity (CPS) |
|---|---|
| 5.2 | 368 |
| 6.9 | 269 |
| 8.8 | 79 |
| 10.1 | 237 |
| 12.5 | 997 |
| 13.5 | 219 |

TABLE XIV-continued

| Peak position (2-Theta) | Intensity (CPS) |
|---|---|
| 14.1 | 117 |
| 14.8 | 801 |
| 15.4 | 820 |
| 16.2 | 447 |
| 17.7 | 194 |
| 18.0 | 514 |
| 19.4 | 119 |
| 20.0 | 913 |
| 21.0 | 155 |
| 21.6 | 386 |
| 22.2 | 305 |
| 23.2 | 290 |
| 24.0 | 188 |
| 24.7 | 308 |
| 26.3 | 1615 |
| 27.1 | 860 |
| 27.5 | 890 |
| 28.2 | 175 |
| 29.9 | 280 |
| 30.4 | 409 |
| 31.2 | 156 |
| 32.0 | 83 |
| 32.8 | 255 |
| 33.1 | 169 |
| 33.9 | 219 |
| 34.6 | 203 |
| 36.4 | 242 |
| 38.2 | 116 |
| 39.6 | 81 |

Of the peaks appearing in the spectrum shown in FIG. 18, Table XV, below lists the 12 most characteristic peaks of the X-ray Powder Diffraction spectrum, expressed in diffraction angle expressed in degrees 2 theta (°2 θ), the corresponding "d" spacing in angstroms (A), and relative intensities of the signal ("RI") in the following notation: S=strong, M=medium, W=weak; V=Very and D=diffuse:

TABLE XV

| Diffraction Angle (°2 θ ± 0.2) | d spacing (A, ±0.04) | relative intensity |
|---|---|---|
| 5.2 | 16.98 | W |
| 6.9 | 12.80 | W |
| 10.1 | 8.75 | W |
| 12.5 | 7.08 | M |
| 14.8 | 5.98 | M |
| 15.4 | 5.75 | M |
| 16.2 | 5.47 | W |
| 20.0 | 4.44 | M |
| 21.6 | 4.11 | W |
| 26.3 | 3.39 | S |
| 27.1 | 3.29 | M |
| 27.5 | 3.24 | M |

Of the peaks characteristic of the tosylate hydrate form I salt form of the compound of Formula I shown in Table XV, the eight most characteristic peaks are those appearing at diffraction angles (in °2 θ) equal to 5.2, 6.9, 12.5, 15.4, 20.0, 26.3, 27.1 and 27.5, and the four most characteristic peaks are those appearing at diffraction angles (in °2 θ) equal to 5.2, 12.5, 20.0 and 26.3.

Figure 19:
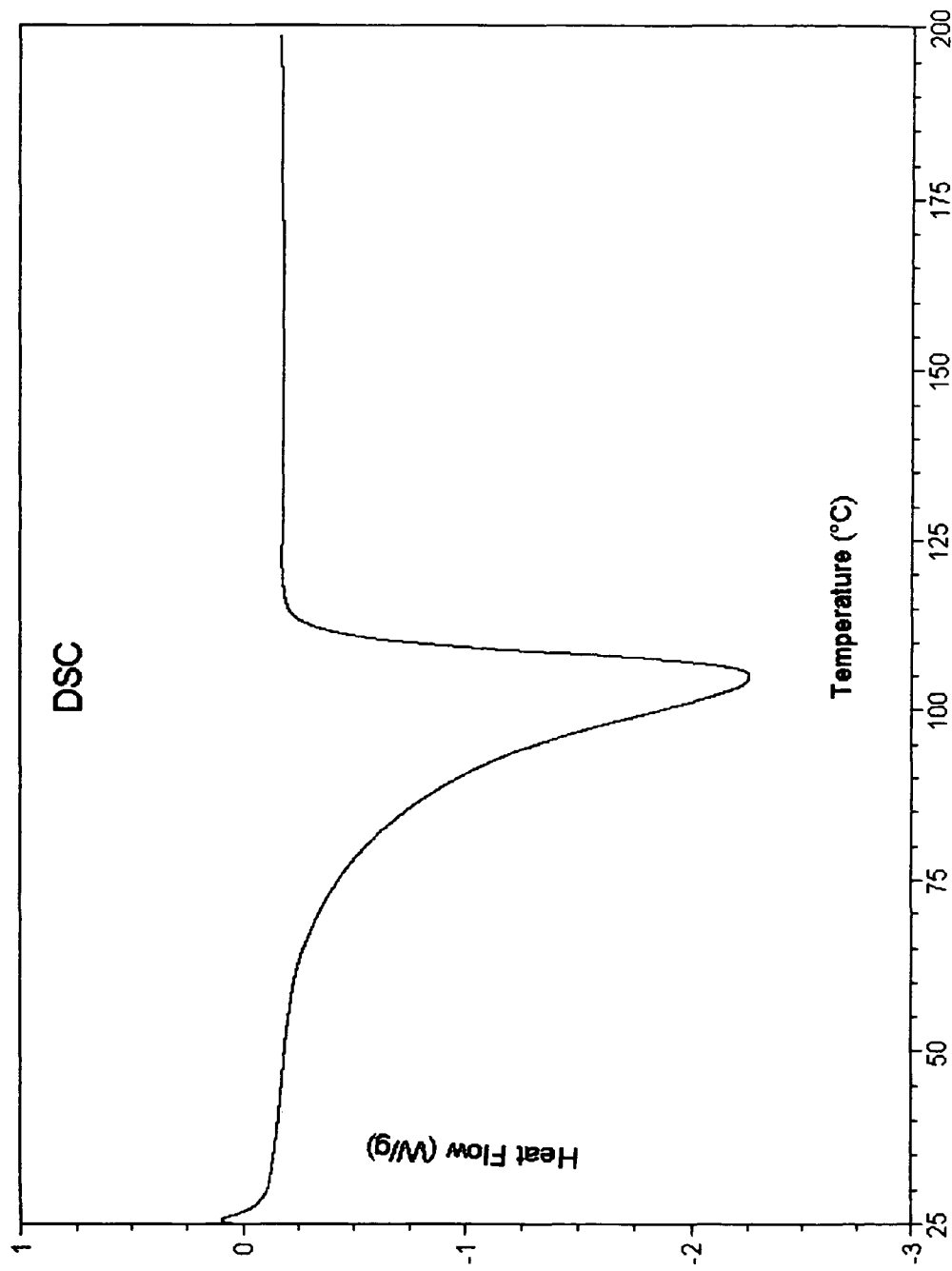
FIG. 19 presents a characteristic differential scanning calorimetry (DSC) thermogram of the crystalline tosylate hydrate form I salt form of the compound of Formula I, [Vertical Axis; Heat Flow in cal/sec/g; Horizontal Axis: Temperature in degrees centigrade].
Figure 20:
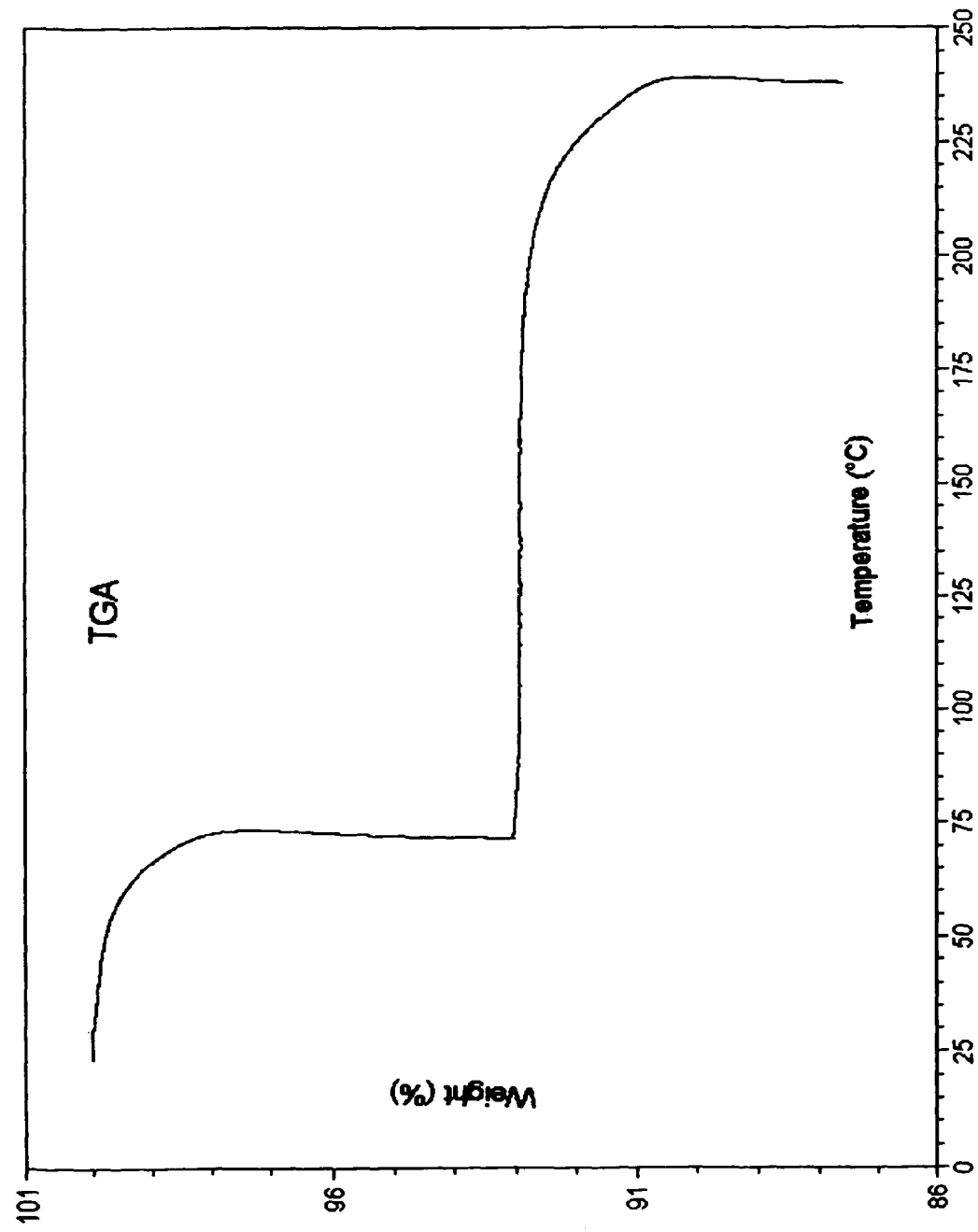
FIG. 20 presents a characteristic thermogravimetric analysis (TGA) of the crystalline tosylate hydrate form I salt form of the compound of Formula I, [horizontal axis; temperature, ° C., vertical axis; percent weight loss in sample].

FIG. 19 illustrates a DSC thermogram of tosylate hydrate form I salt form of the compound of Formula I, obtained in accordance with the above-described procedures, and FIG. 20 illustrates thermogravimetric analysis of the tosylate hydrate form I salt. The DSC analysis shows that the tosylate hydrate form I salt gives a broad endotherm from 50 to 120° C. with peaking at about 105° C., which corresponds to the dehydration of the tosylate hydrate form 1 salt. A weight loss of about 8% was observed in the TGA at the same temperature range, which corresponds to about 3 water molecules/molecule of salt.

Preparation of Tosylate Hydrate Form 2 Salt Form of the Compound of Formula I

An aliquot (1.5 g, 2.2 mmol) of the tosylate anhydrous form 1 salt form of the compound of Formula I prepared above was dissolved in 4.5 mL of methanol. The solution was concentrated to dryness after 3 days by vacuum distillation. The solids were slurried in 4.5 mL of 2-propanol which was shaken at 25° C. and 350 RPM for six days yielding precipitate. The solids were collected by vacuum filtration and dried under vacuum at room temperature over a 12 hour period. The resulting crystalline tosylate hydrate form 2 salt form of the compound of Formula I was analyzed by X-ray crystallography (FIG. 21), DSC (FIG. 22), and TGA (FIG. 23) in accordance with the procedures described above.

Figure 21:
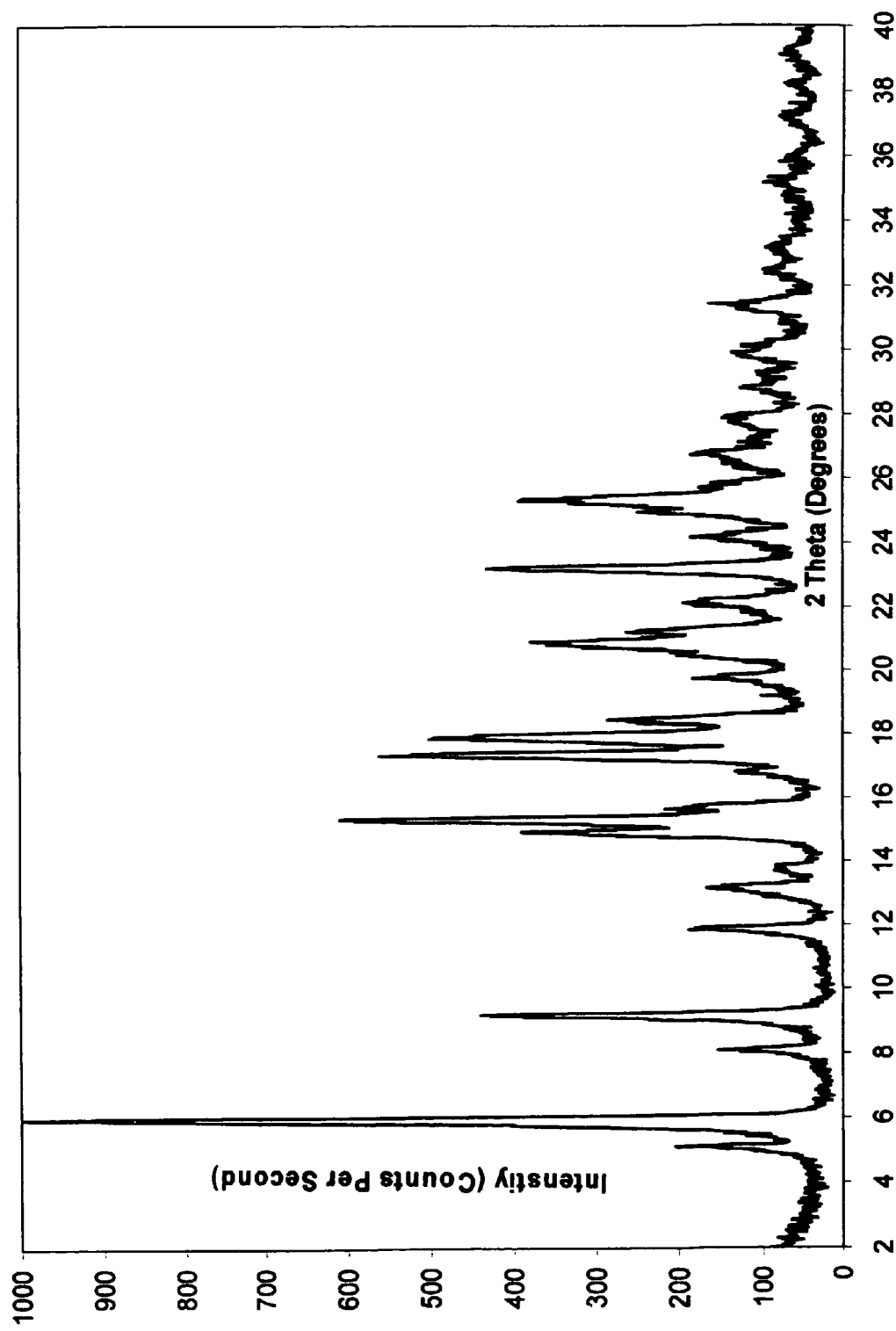
FIG. 21 presents a characteristic x-ray powder diffraction pattern of the crystalline tosylate hydrate form II salt form of the compound of Formula I [Vertical Axis: Intensity CPS, counts (square root)); Horizontal Axis: Two Theta (degrees)].

The X-ray powder diffraction spectrum obtained on a sample of the above-prepared crystalline fumarate salt form appearing in FIG. 21 exhibits absorption peaks at the following diffraction angles having the intensity shown in Table XX:

TABLE XX

| Peak position (2-Theta) | Intensity (CPS) |
|---|---|
| 5.1 | 150 |
| 5.7 | 302 |
| 5.9 | 1037 |
| 8.1 | 110 |
| 9.2 | 442 |
| 11.9 | 175 |
| 13.1 | 140 |
| 14.9 | 363 |
| 15.3 | 632 |
| 15.6 | 177 |
| 17.3 | 545 |
| 17.9 | 465 |
| 18.4 | 237 |
| 19.7 | 105 |
| 20.5 | 130 |
| 20.8 | 315 |
| 21.2 | 188 |
| 22.1 | 127 |
| 23.2 | 405 |
| 24.1 | 103 |
| 25.0 | 167 |
| 25.3 | 322 |
| 26.7 | 108 |

Of the peaks appearing in the tosylate hydrate form 2 salt form of the compound of Formula I spectrum shown in FIG. 21, Table XVI below lists the 12 most characteristic absorption peaks at diffraction angles and relative intensity shown in Table XVI, below. Table XVI lists also the calculated lattice spacing determined from the x-ray data in FIG. 21. In Table XVI diffraction angle is expressed in degrees 2 theta (°2 θ), the corresponding "d" spacing in angstroms (A), and relative intensities of the signal ("RI") in the following notation: S=strong, M=medium, W=weak; V=Very and D=diffuse:

TABLE XVI

| Diffraction Angle (°2 θ ±0.2) | d spacing (A, ±0.04) | relative intensity |
|---|---|---|
| 5.7 | 15.49 | M |
| 5.9 | 14.97 | VS |
| 9.2 | 9.60 | M |

TABLE XVI-continued

| Diffraction Angle (°2 θ ±0.2) | d spacing (A, ±0.04) | relative intensity |
|---|---|---|
| 11.9 | 7.43 | W |
| 14.9 | 5.94 | M |
| 15.3 | 5.79 | S |
| 17.3 | 5.12 | S |
| 17.9 | 4.95 | M |
| 18.4 | 4.82 | W |
| 20.8 | 4.27 | MB |
| 23.2 | 3.83 | M |
| 25.3 | 3.52 | MB |

Of the peaks characteristic of the tosylate hydrate form I salt form of the compound of Formula I shown in Table XVI, the eight most characteristic peaks are those appearing at diffraction angles (in °2 θ) equal to 5.9, 9.2, 11.9, 14.9, 17.4, 20.8, 23.2, and 15.3, and the four most characteristic peaks are those appearing at diffraction angles (in °2 θ) equal to 5.9, 9.2, 11.9, and 14.9.

Figure 22:
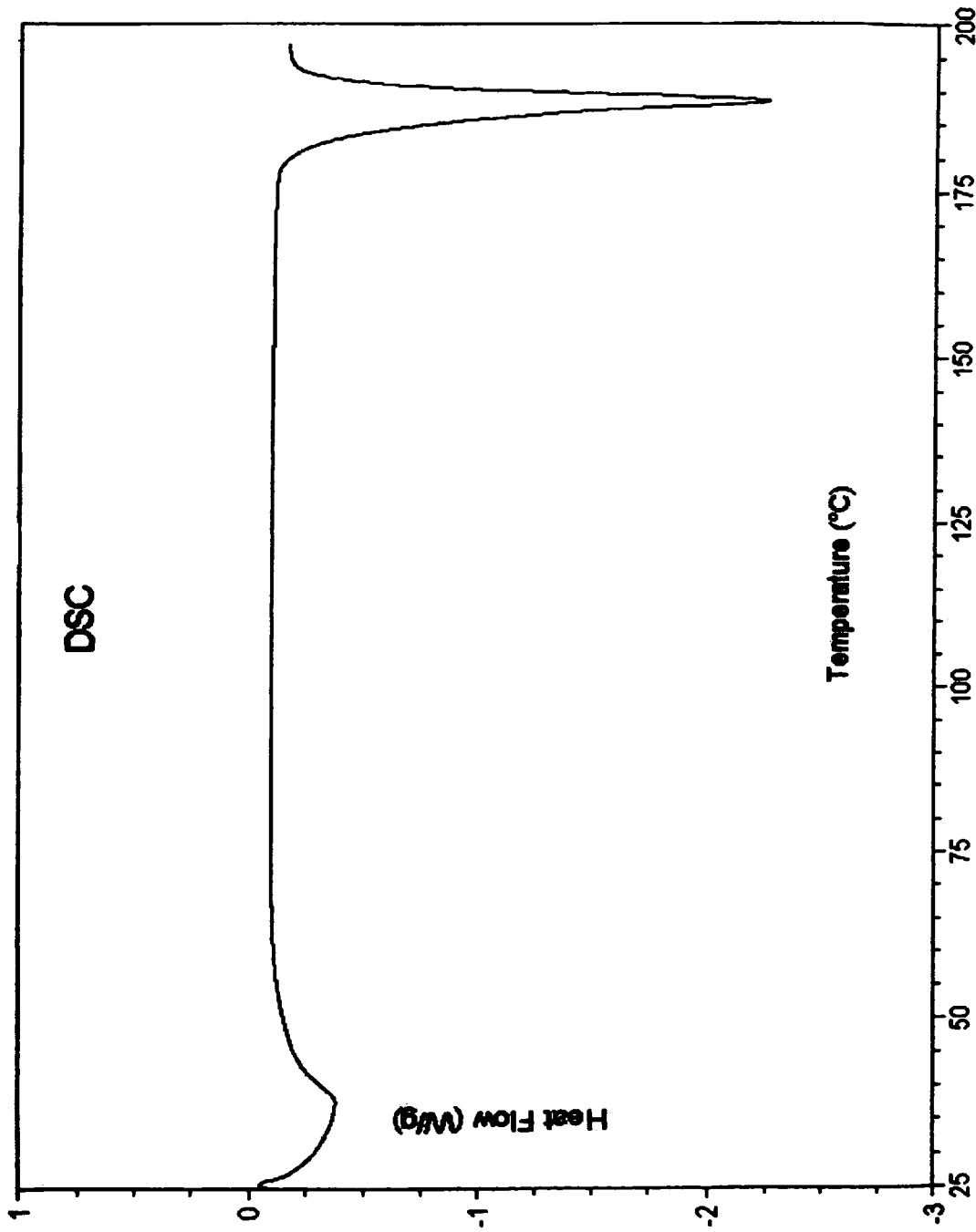
FIG. 22 presents a characteristic differential scanning calorimetry (DSC) thermogram of the crystalline tosylate hydrate form II salt form of the compound of Formula II, [Vertical Axis; Heat Flow in cal/sec/g; Horizontal Axis: Temperature in degrees centigrade].
Figure 23:
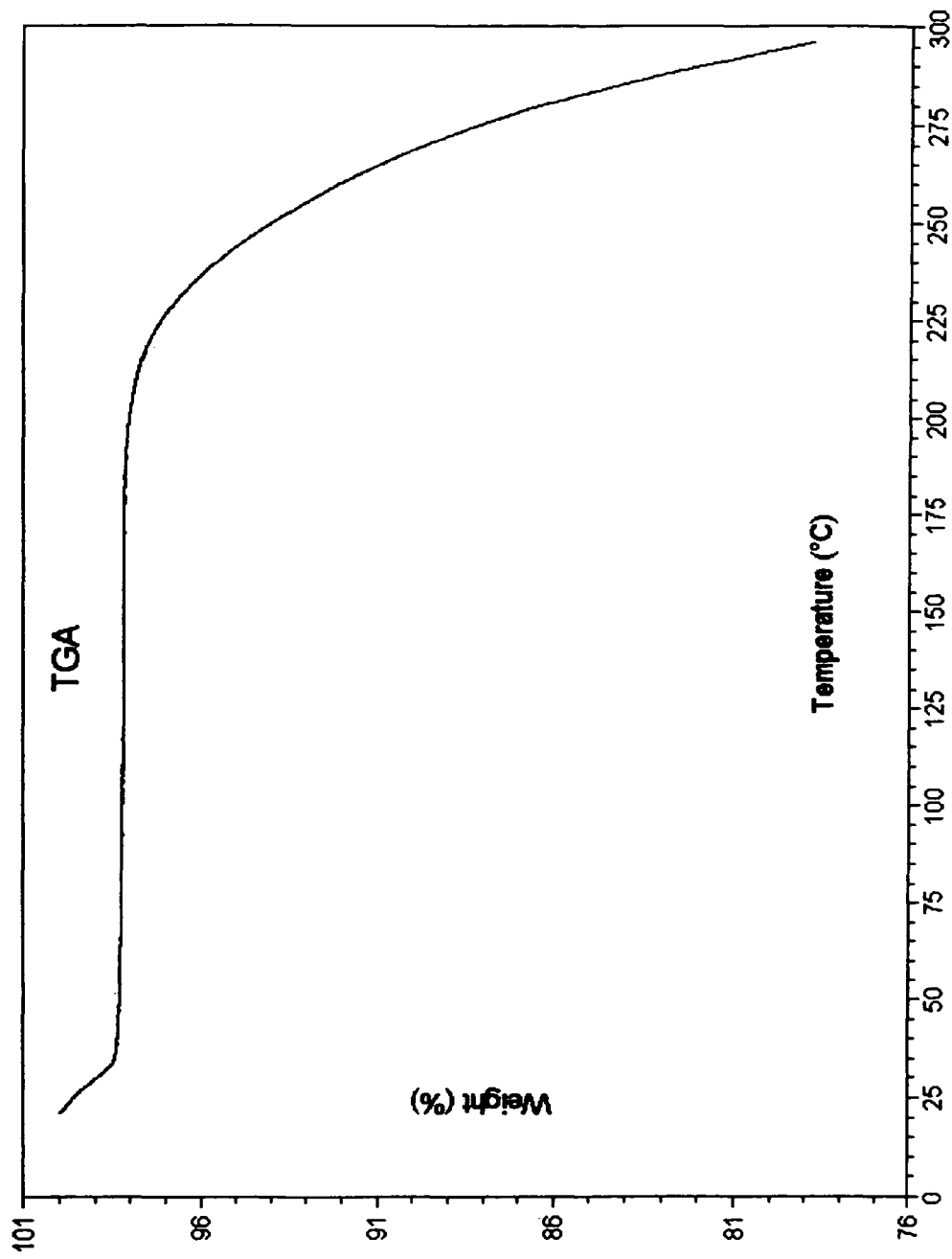
FIG. 23 presents a characteristic thermogravimetric analysis (TGA) of the crystalline tosylate hydrate form II salt form of the compound of Formula I, [horizontal axis; temperature, ° C., vertical axis; percent weight loss in sample].

FIG. 22 illustrates a DSC thermogram of tosylate hydrate form 2 salt form of the compound of Formula I, obtained in accordance with the above-described procedures, and FIG. 23 illustrates thermogravimetric analysis of the tosylate hydrate form 2 salt. The DSC analysis is consistent with the sample being a hydrate and not a solvate, having a single sharp melting point at about 185° C. The TGA shows no significant weight loss below the melting point of the compound, with decomposition after that, consistent with a non-solvate crystalline salt form.

Preparation of Oxalate Form I Salt Form of the Compound of Formula I

An aliquot of the compound of Formula I (free base form, 11.0 g, 21.1 mmol) was suspended in 300 ml of ethanol. The suspension was heated to 60° C. Oxalic acid (3.2 g, 25.4 mmol, 1.2 eq) was added to the suspension and the mixture was heated to 75° C., with stirring, and held at 75° C. for one hour, providing a solution. The solution was cooled to a temperature of 10° C. over a one hour period, precipitating solids. The solids were collected by vacuum filtration washed with ethanol and dried in a vacuum oven at 100° C. for five hours, to give 9.0 g (69.6%) of white needles.

The dried crystals of the oxalate form I salt form of the compound of Formula I were analyzed by X-ray powder diffraction spectroscopy (FIG. 24), differential scanning calorimetry (FIG. 25) and thermogravimetric analysis (FIG. 26) according the above-described procedures.

The X-ray powder diffraction spectroscopy obtained on a sample of the oxalate form I salt (FIG. 24) exhibits absorption peaks at the following diffraction angles having the intensity shown in Table XVII:

TABLE XVII

| Peak position (2-Theta) | Intensity (CPS) |
|---|---|
| 6.8 | 2302 |
| 7.6 | 660 |
| 9.3 | 1094 |
| 11.3 | 107 |
| 13.7 | 153 |
| 14.9 | 1397 |
| 15.7 | 263 |
| 16.1 | 224 |
| 17.6 | 184 |
| 18.6 | 3801 |
| 19.4 | 214 |
| 19.9 | 130 |

TABLE XVII-continued

| Peak position (2-Theta) | Intensity (CPS) |
|---|---|
| 21.5 | 262 |
| 22.3 | 300 |
| 22.7 | 454 |
| 24.7 | 150 |
| 25.4 | 111 |
| 26.0 | 216 |
| 26.7 | 742 |
| 27.7 | 354 |
| 28.5 | 161 |
| 29.8 | 140 |
| 33.6 | 195 |
| 34.2 | 376 |
| 37.5 | 215 |
| 37.8 | 184 |

Figure 24:
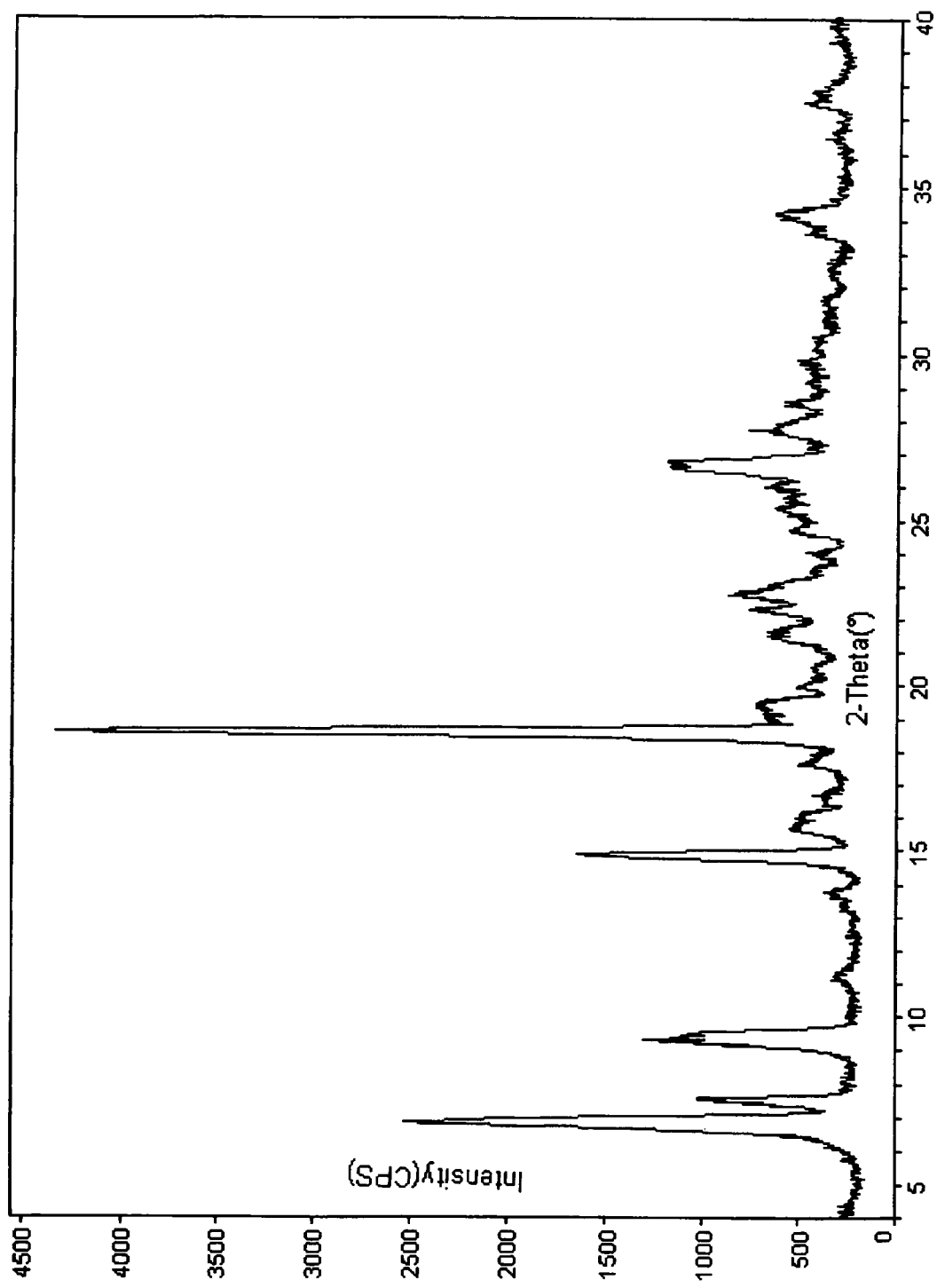
FIG. 24 presents a characteristic x-ray powder diffraction pattern of the crystalline oxalate form I salt form of the compound of Formula I [Vertical Axis: Intensity CPS, counts (square root)); Horizontal Axis: Two Theta (degrees)].
Figure 25:
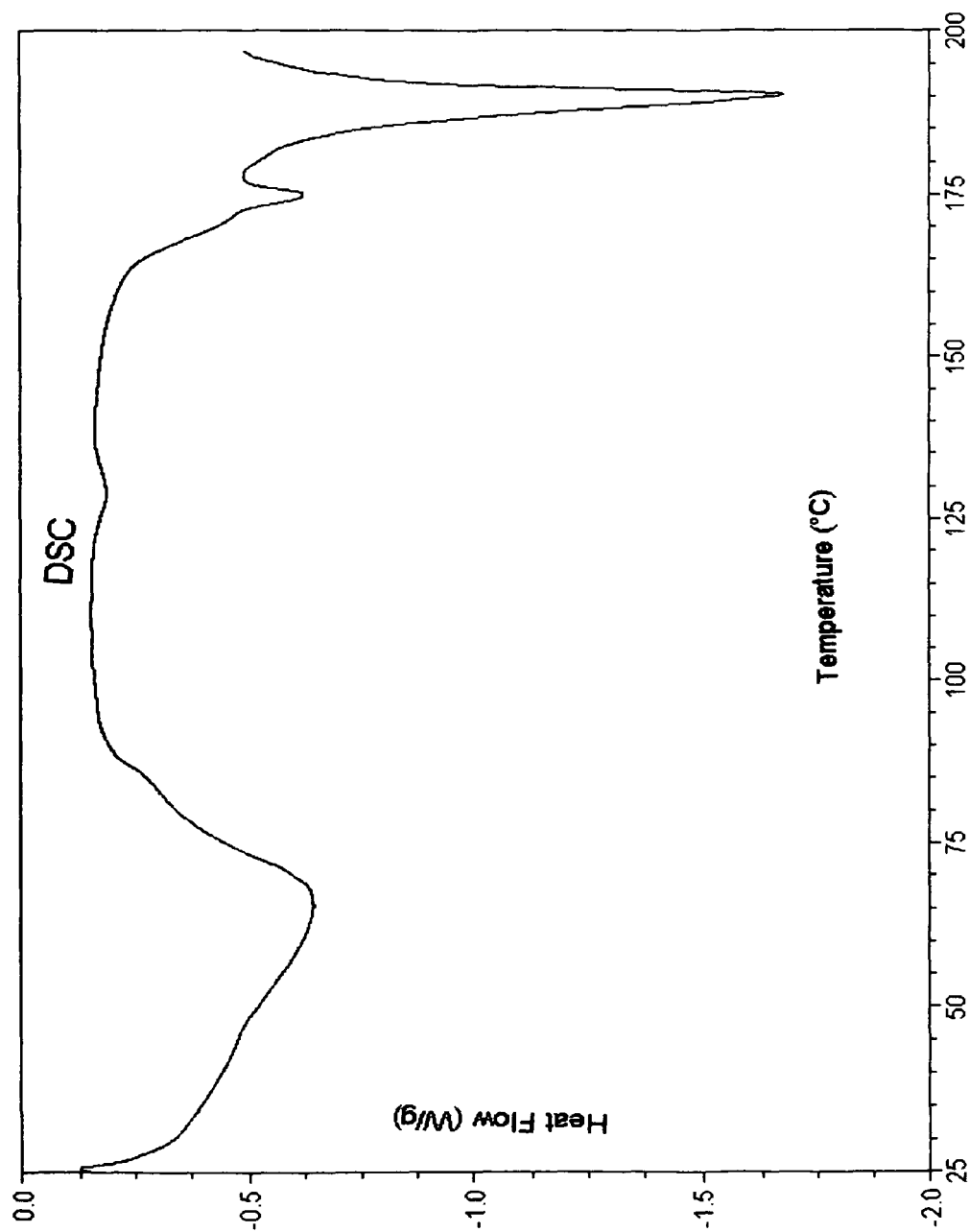
FIG. 25 presents a characteristic differential scanning calorimetry (DSC) thermogram of the crystalline oxalate form I salt form of the compound of Formula II, [Vertical Axis; Heat Flow in cal/sec/g; Horizontal Axis: Temperature in degrees centigrade].

Of the peaks appearing in the spectrum shown in FIG. 24, Table XVIII, below lists the 12 most characteristic peaks of the X-ray Powder Diffraction spectrum, expressed in diffraction angle expressed in degrees 2 theta (°2 θ), the corresponding "d" spacing in angstroms (A), and relative intensities of the signal ("RI") in the following notation: S=strong, M=medium, W=weak; V=Very and D=diffuse:

TABLE XVIII

| Diffraction Angle (°2 θ ±0.2) | d spacing (A, ±0.04) | relative intensity |
|---|---|---|
| 6.8 | 12.99 | VS |
| 7.6 | 11.62 | M |
| 9.3 | 9.50 | S |
| 11.3 | 7.82 | W |
| 14.9 | 5.94 | S |
| 17.6 | 5.03 | W |
| 18.6 | 4.69 | VS |
| 19.4 | 4.57 | W |
| 19.9 | 4.46 | W |
| 22.7 | 3.91 | WD |
| 26.7 | 3.34 | M |
| 34.2 | 2.62 | W |

Of the peaks characteristic of the oxalate form I salt of the compound of Formula I shown in Table XVIII, the eight most characteristic peaks are those appearing at diffraction angles (in °2 θ equal to 6.8, 7.6, 9.3, 14.9, 18.9, 22.7, 26.7, and 34.2, and the four most characteristic peaks are those appearing at diffraction angles (in °2 θ) equal to 6.8, 9.3, 14.9, and 18.6.

Figure 26:
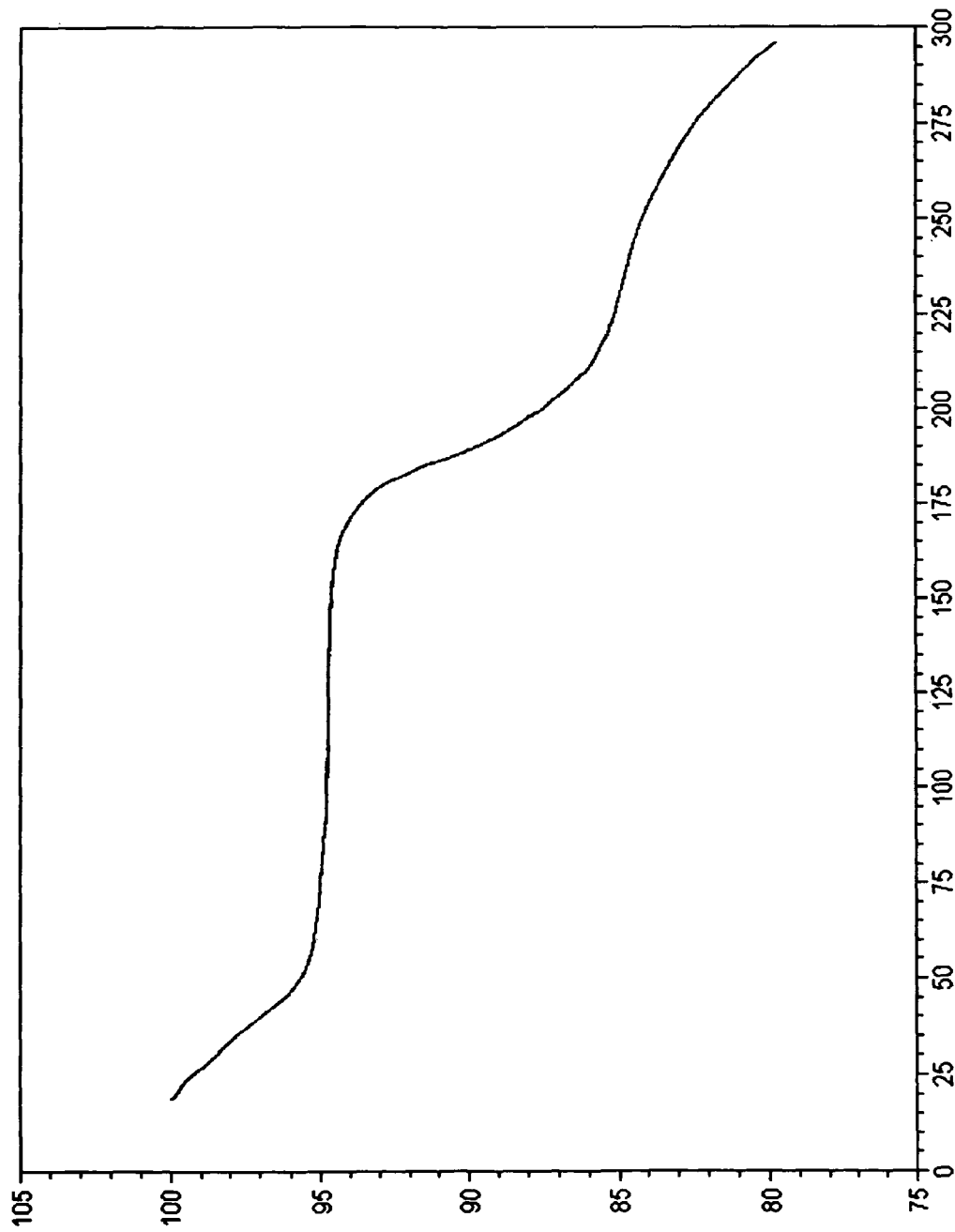
FIG. 26 presents a characteristic thermogravimetric analysis (TGA) of the crystalline oxalate form I salt form of the compound of Formula I, [horizontal axis; temperature, ° C., vertical axis; percent weight loss in sample].

FIG. 26 illustrates a DSC thermogram of the oxalate form I salt form of the compound of Formula I, obtained in accordance with the above-described procedures, and FIG. 6 illustrates thermogravimetric analysis of the oxalate anhydrous form I salt. The DSC analysis indicates that the oxalate anhydrous form I salt is desolvated over the range of 25° C. to 85° C. The TGA analysis shows that the material undergoes a 5% weight loss over this temperature range, which corresponds to approximately 1 equivalent of methanol solvate based on the amount of the compound of Formula I present in the crystal.

The crystalline oxalate salt form of the compound of Formula I prepared above was investigated for photo stability in accordance with ICH-photostability conditions. Samples of the salt exposed to one cycle of ICH photostability conditions did not show any significant degradation.

What is claimed is:

1. An isolated amount of a crystalline salt form of compound I selected from a crystalline maleate monohydrate salt form I, crystalline tosylate hydrate salt form I, a crystalline fumarate salt form having the X-ray powder diffraction pattern characteristic of FIG. 12, and a crystalline oxalate salt form having the X-ray powder diffraction pattern characteristic of FIG. 24

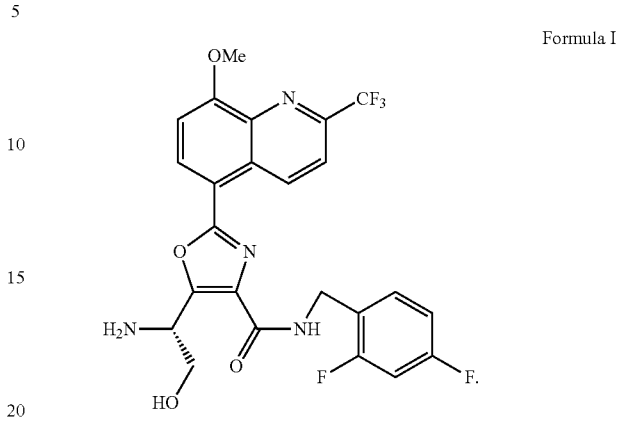

Formula I

2. The crystalline salt form of claim 1 wherein the salt form is crystalline maleate monohydrate salt form I.

3. A process for making a crystalline maleate monohydrate salt form of the compound of Formula I:

Formula I the process comprising:
(a) suspending an aliquot of the free base compound of Formula I in a mixed isopropanol/water solvent comprising at least 50 vol % i-propanol, wherein the ratio of suspended material to solvent is at least about 1:8 weight in g/vol in ml;
(b) heating the suspension prepared in step "a" to at least 50° C.;
(c) admixing over a 10 minute period with the heated suspension prepared in Step "b" a solution made by dissolving at least one equivalent of maleic acid in sufficient amount of a mixed solvent to dissolve it, the mixed solvent comprising 50% by volume i-propanol and 50% by volume water;
(d) filtering the admixture from Step "c" to provide a solution while maintaining the temperature of the solution at a temperature of at least about 50° C.;
(e) adding over a 10 minute period to the filtrate from Step "d" additionally about 1.25 volumes of water based on the volume of water used in Step "a" while maintaining the mixture at a temperature of at least about 50° C.;
(f) cooling the solution from Step "e" to about 40° C. over 30 minutes, thereby forming a precipitate slurry;

(g) stirring the slurry from Step "f" for a first period of time at a temperature of about 40° C., followed by cooling the slurry to 5° C. over a 2 hour period;

(h) optionally collecting the solids precipitated in Step "g" and washing them in a mixed isopropanol/water solvent containing at least 66% isopropanol by volume;

(i) optionally drying the solids obtained in step "h" in a vacuum oven for 5 hours at 55 ° C.

4. The crystalline maleate monohydrate salt form I of the maleate salt of 5-(1(S)-amino-2-hydroxyethyl)-N-[(2,4-difluorophenyl)-methyl]-2-[8-methoxy-2-(trifluoromethyl)-5-quinoline]-4-oxazolecarboxamide in isolated amount, characterized by the infrared spectrum of FIG. 10, and further characterized by the X-ray powder diffraction pattern shown in Table I expressed in terms of diffraction angle (in 2θ, all values reflect an accuracy of ±0.2) lattice "d" spacing (in angstroms) and relative peak intensities("RI"):

TABLE I

| Diffraction angle (2θ, ±0.2) | RI | Lattice Spacing (Å ± 0.04) |
|---|---|---|
| 6.5 | Strong | 13.59 |
| 7.5 | Very Strong | 11.78 |
| 21.2 | Very Strong | 4.19 |
| 27.2 | Very Strong | 3.28. |

5. A process for making crystalline tosylate hydrate salt form I of the compound of Formula I

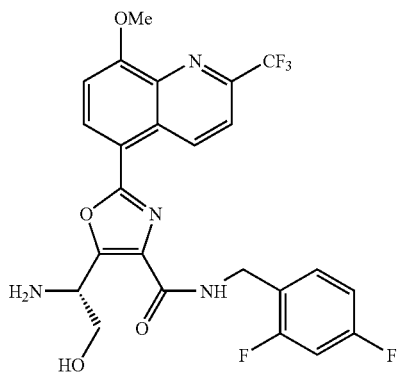

Formula I the process comprising:

(a) preparing a crystalline tosylate anhydride salt by:
  (1) suspending an aliquot of the free base compound of Formula I in at least 10 ml of acetonitrile/ g of the compound of Formula I suspended;
  (2) heating the suspension prepared in Step "a" to a temperature of at least about 60° C.;
  (3) mixing at least one equivalent of toluenesulfonic acid into the suspension;
  (4) heating the mixture prepared in Step "c" to at least about 70° C. yielding a solution;
  (5) mixing t-butylmethyl ether into the hot solution prepared in Step "d" over a period of at least about 20 minutes in an amount that provides a ratio of 13:8 acetonitrile:t-butylmethylether in the mixture; and
  (6) cooling the mixture to ambient temperature over a period of at least about 2 hours precipitating the crystalline anhydrous tolysulfonate salt of the compound of Formula I;

(b) collecting an aliquot of the precipitate salt prepared in Step "a(6)" and combining it with an amount of water to give a ratio of 6 ml of water/g of salt for a period of time necessary to produce a first solid scum;

(c) slurrying first solid scum produced in Step "b" with an amount of water equal to 1.66× the amount of water used in Step "b";

(d) agitating the slurry prepared in Step "c" for a period of time necessary to produce a wet cake;

(e) adding an additional 3× the amount of water added in Step "c" to form a second slurry with the wet cake produced in Step "d" and agitating the slurry for 5 days;

(f) drying the solids from the slurry produced in Step "e" under vacuum at ambient temperature, thereby producing the tosylate hydrate Form I salt form of the compound of Formula I.

6. The crystalline tosylate hydrate salt Form I of 5-(1(S)-amino-2-hydroxyethyl)-N-[(2,4-difluorophenyl)-methyl]-2-[8-methoxy-2-(trifluoromethyl)-5-quinoline]-4-oxazolecarboxamide compound of Formula IV isolated from the process of claim 5,

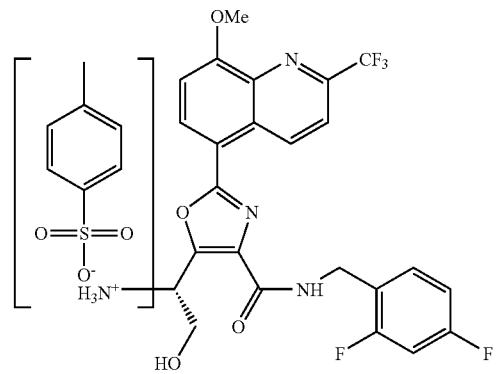

Figure 11A:
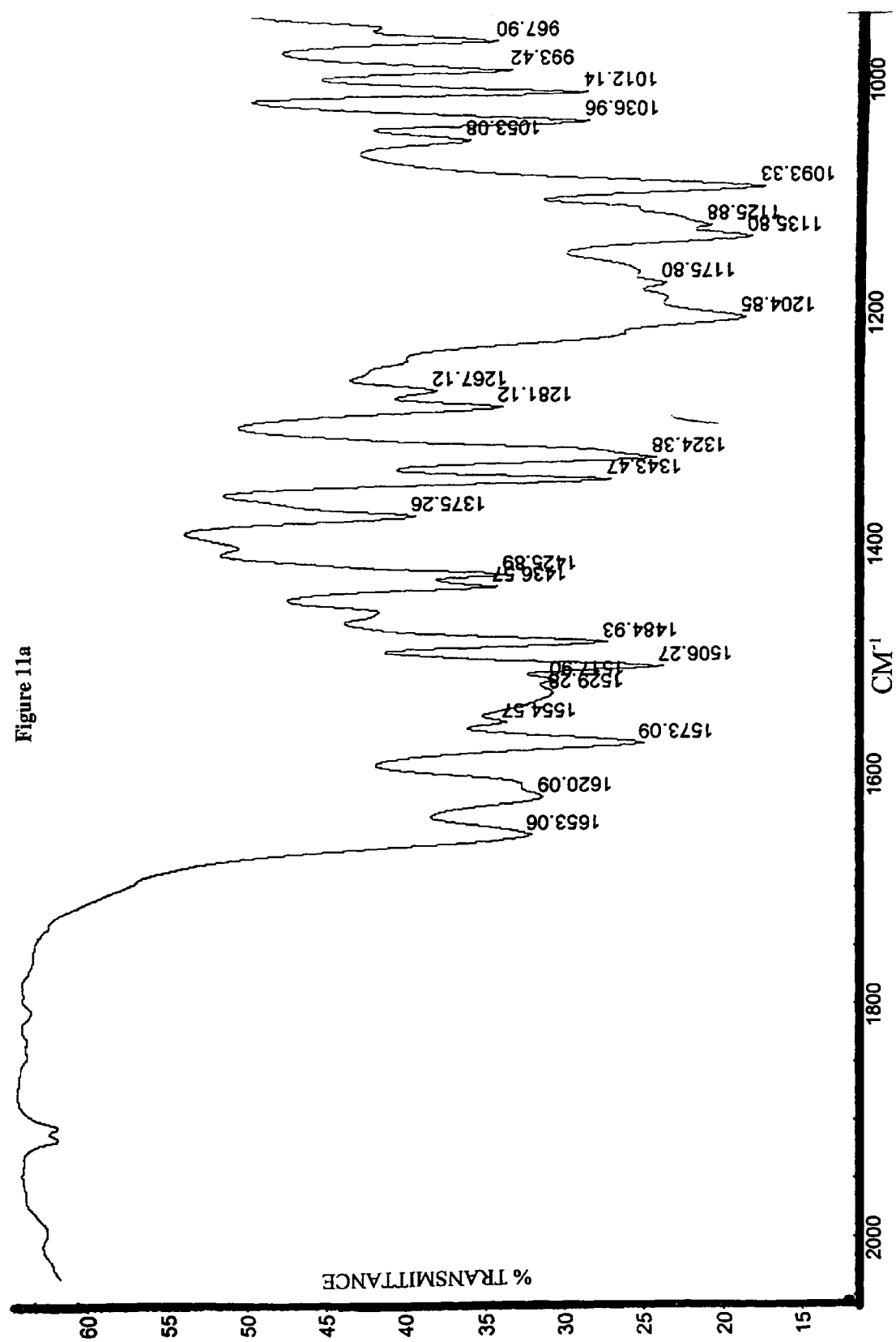
FIGS. 11a to 11c present a characteristic infrared spectrum pattern of the crystalline tosylate hydrate form I salt form of the compound of Formula I, with FIG. 11a containing the spectrum over the region from 2000 cm$^{-1}$ to 1000 cm$^{-1}$.
Figure 11B:
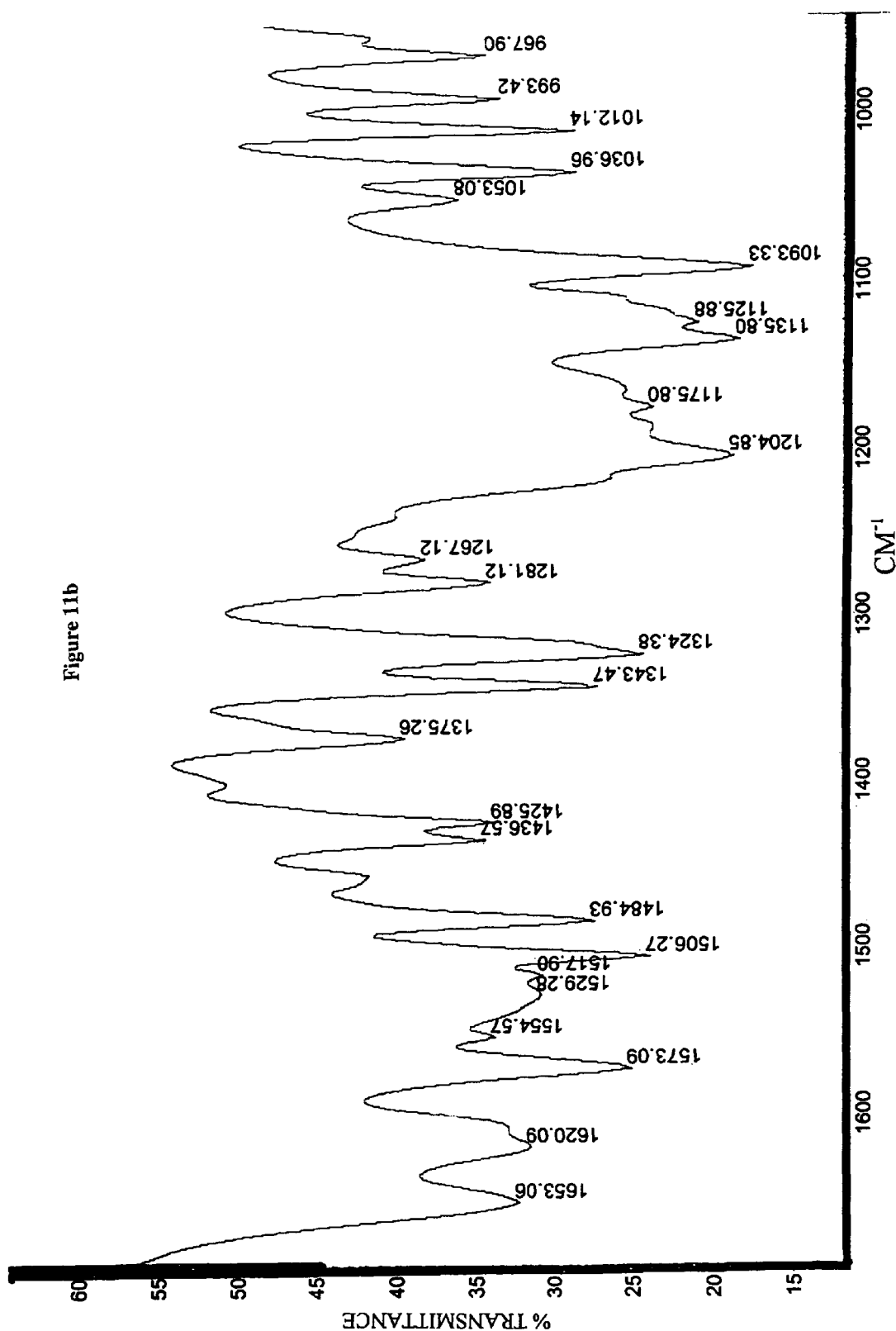
Figure 11C:
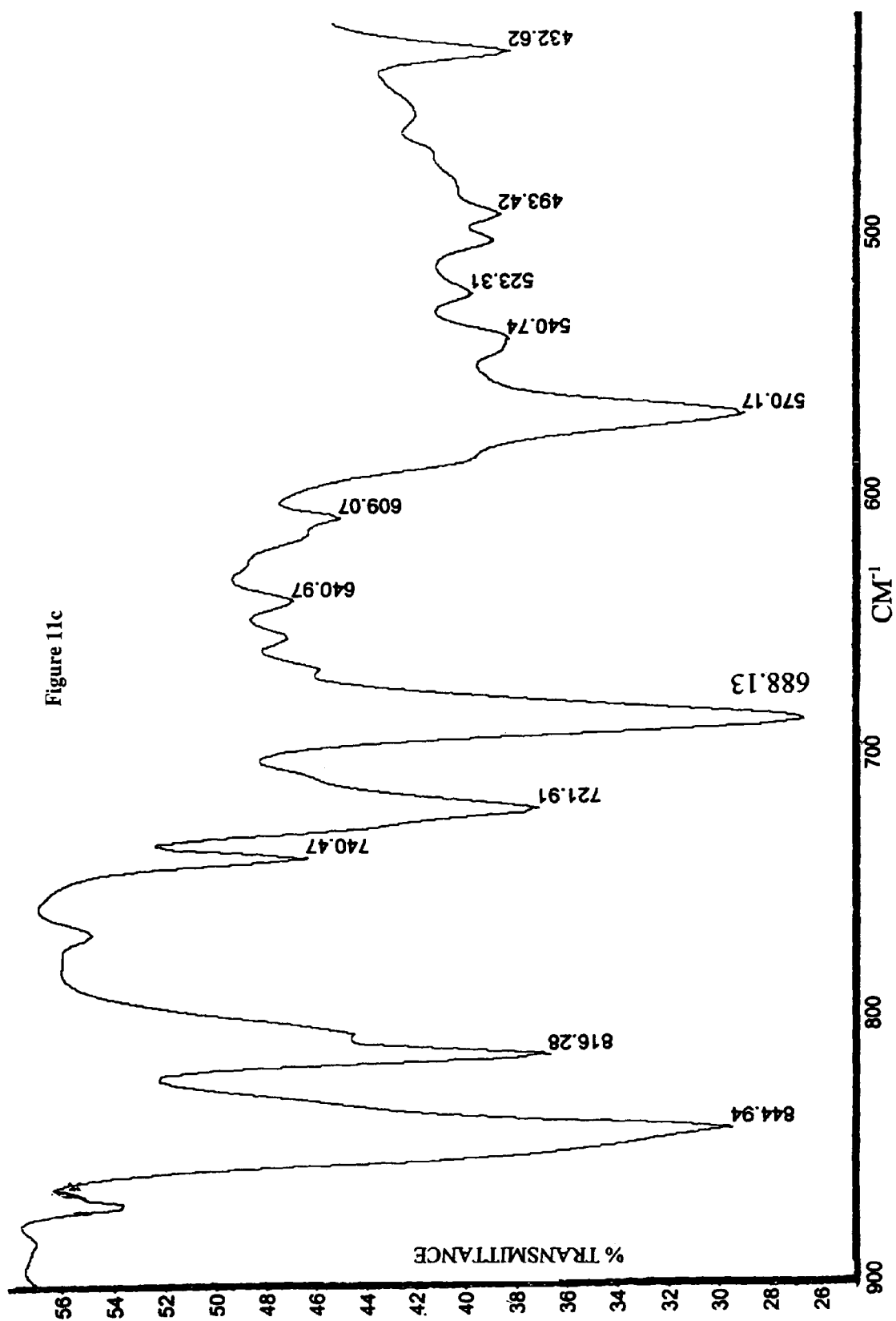

Formula IV said crystalline tosylate hydrate salt form I being characterized by the Infrared Spectrum schematically illustrated in FIG. 11 and by the X-ray powder diffraction pattern shown in Table II expressed in terms of diffraction angle (in 2θ, all values reflect an accuracy of ±0.2) lattice "d" spacing (in angstroms) and relative peak intensities("RI"):

TABLE II

| Diffraction angle (2θ, ±0.2) | RI | Lattice Spacing (Å ± 0.04) |
|---|---|---|
| 5.2 | Weak | 16.98 |
| 12.5 | Medium | 7.08 |
| 20.0 | Weak | 4.44 |
| 26.3 | Strong | 3.39. |

7. A process for making a crystalline fumarate salt form of 5-(1(S)-amino-2-hydroxyethyl)-N-[(2,4-difluorophenyl)-methyl]-2-[8-methoxy-2-(trifluoromethyl)-5-quinoline]-4-oxazolecarboxamide fumarate salt compound having the structure of Formula V),

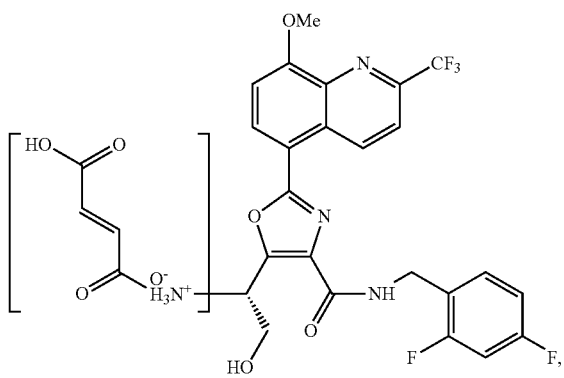

Formula V the process comprising:
- (a) suspending an aliquot of the free base compound having the structure of Formula I in 50 ml of acetonitrile;
- (b) heating the suspension formed in Step "a" to about 60° C.;
- (c) mixing with the heated suspension at least one equivalent of fumaric acid;
- (d) heating the mixture prepared in Step "c" to a temperature at which the suspended materials are dissolved;
- (e) cooling the solution prepared in Step "d" to ambient temperature over a period of about 2 hours to provide a precipitate; and
- (f) collecting the precipitate and drying it in a vacuum oven at a temperature of about 50° C.;

said crystalline fumarate salt form thus produced having an X-ray powder diffraction pattern yielding the following values, expressed in terms of diffraction angle (in 2θ, all values reflect an accuracy of ±0.2) lattice "d" spacing (in angstroms) and relative peak intensities("RI"):

| Diffraction angle (2θ, ±0.2) | RI | Lattice Spacing (Å ± 0.04) |
|---|---|---|
| 8.0 | Strong | 11.04 |
| 19.9 | Medium | 4.46 |
| 22.5 | Medium | 3.95 |
| 25.6 | Medium | 3.48. |

8. The process of claim 7 wherein in said heating Step "d" the mixture is heated to temperature of at least about 80° C. and in cooling Step "e" ambient temperature is about 25° C.

9. Crystalline fumarate salt isolated from the process of claim 7.

10. The crystalline maleate monohydrate salt form I of claim 4 wherein the salt form is made from the maleate salt compound of Formula II produced by the process of claim 3

Formula II

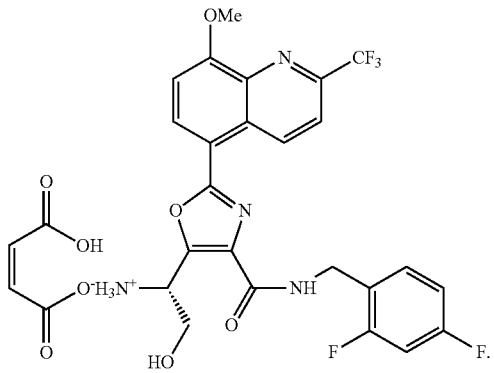

* * * * *